United States Patent
Schramm et al.

(10) Patent No.: US 11,186,575 B2
(45) Date of Patent: Nov. 30, 2021

(54) TREATMENT OF HELICOBACTER PYLORI INFECTIONS

(71) Applicants: Albert Einstein College of Medicine, Inc., Bronx, NY (US); Victoria Link Limited, Wellington (NZ)

(72) Inventors: Vern L. Schramm, New Rochelle, NY (US); Shanzhi Wang, Bronx, NY (US); Antti Marko Haapalainen, Oulu (FI); Gary Brian Evans, Lower Hutt (NZ); Richard Hubert Furneaux, Wellington (NZ); Keith Clinch, Lower Hutt (NZ); Peter Charles Tyler, Wellington (NZ); Shivali Ashwin Gulab, Wellington (NZ)

(73) Assignees: Alber Einslein College of Medicine, Bronx, NY (US); Victoria Link Limited, Wellington (NZ)

( * ) Notice: Subject to any disclaimer, the term of this patent is extended or adjusted under 35 U.S.C. 154(b) by 0 days.

(21) Appl. No.: 14/419,669

(22) PCT Filed: Aug. 7, 2013

(86) PCT No.: PCT/US2013/053885
§ 371 (c)(1),
(2) Date: Feb. 5, 2015

(87) PCT Pub. No.: WO2014/025842
PCT Pub. Date: Feb. 13, 2014

(65) Prior Publication Data
US 2015/0210701 A1 Jul. 30, 2015

Related U.S. Application Data

(60) Provisional application No. 61/806,476, filed on Mar. 29, 2013, provisional application No. 61/680,334, filed on Aug. 7, 2012.

(51) Int. Cl.
C07D 487/04 (2006.01)
A61P 31/04 (2006.01)
A61K 31/519 (2006.01)

(52) U.S. Cl.
CPC .......... C07D 487/04 (2013.01); A61K 31/519 (2013.01); A61P 31/04 (2018.01); Y02A 50/30 (2018.01)

(58) Field of Classification Search
CPC .............................. C07D 487/04; A61K 31/519
See application file for complete search history.

(56) References Cited

U.S. PATENT DOCUMENTS

| | | | |
|---|---|---|---|
| 5,985,848 A | 11/1999 | Furneaux et al. | |
| 6,066,722 A | 5/2000 | Furneaux et al. | |
| 6,228,847 B1 | 5/2001 | Furneaux et al. | |
| 6,492,347 B2 | 12/2002 | Furneaux et al. | |
| 6,803,455 B2 | 10/2004 | Furneaux et al. | |
| 7,098,334 B2 | 8/2006 | Furneaux et al. | |
| 7,211,653 B2 | 5/2007 | Furneaux et al. | |
| 7,390,890 B2 | 6/2008 | Furneaux et al. | |
| 7,553,839 B2 | 6/2009 | Furneaux et al. | |
| 8,173,662 B2 | 5/2012 | Furneaux et al. | |
| 8,183,019 B2 | 5/2012 | Lenz et al. | |
| 8,283,345 B2 | 10/2012 | Furneaux et al. | |
| 8,383,636 B2 | 2/2013 | Evans et al. | |
| 8,541,567 B2 | 9/2013 | Schramm | |
| 8,853,224 B2 | 10/2014 | Clinch et al. | |
| 9,290,501 B2 | 3/2016 | Schramm et al. | |
| 9,493,465 B2 | 11/2016 | Evans et al. | |
| 9,522,159 B2 | 12/2016 | Schramm et al. | |
| 10,118,928 B2 | 11/2018 | Schramm et al. | |
| 2006/0160765 A1 | 7/2006 | Evans et al. | |
| 2006/0217551 A1* | 9/2006 | Evans ................ | C07H 19/23 544/280 |
| 2010/0105708 A1 | 4/2010 | Jakel et al. | |
| 2011/0046167 A1 | 2/2011 | Clinch et al. | |
| 2011/0190265 A1 | 8/2011 | Schramm | |
| 2012/0157479 A1 | 6/2012 | Evans et al. | |
| 2013/0274220 A1 | 10/2013 | Schramm et al. | |
| 2015/0210701 A1 | 7/2015 | Schramm et al. | |

(Continued)

FOREIGN PATENT DOCUMENTS

WO 2015123101 A1 8/2015

OTHER PUBLICATIONS

Gutierrez et al. (Nature Chem. Biol., 2009 5(4), pp. 251-257).*

(Continued)

*Primary Examiner* — Susanna Moore
(74) *Attorney, Agent, or Firm* — Amster Rothstein & Ebenstein LLP

(57) ABSTRACT

Methods of treating infections due to *Helicobacter pylori* (*H. pylori*), in particular in subjects having a peptic ulcer, are disclosed where the methods comprise administering to the subject an inhibitor of *H. pylori* MTAN (5'-methylthioadenosine nucleosidase) having the structure of formula (I)

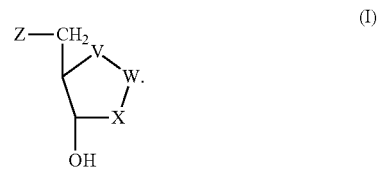

(I)

6 Claims, 4 Drawing Sheets

(56) References Cited

U.S. PATENT DOCUMENTS

2015/0274741 A1    10/2015   Evans et al.
2017/0166571 A1     6/2017   Schramm et al.

OTHER PUBLICATIONS

Gutierrez et al. (ACS Chemical Biology, 2007, 2(11), pp. 725-734, published online Nov. 16, 2007).*
Gutierrez et al. (Nature Chemical Biology, 2009, 5(4), pp. 251-257).*
Wang et al. (Biochemistry, 2012, 51(35), pp. 6892-6894).*
Gutierrez et al. (ACS Chemical Biology, 2007, 2(11), pp. 725-734).*
PCT International Search Report and Written Opinion, dated Dec. 23, 2013 in connection with PCT International Application No. PCT/US2013/53885, 10 pages.
Li X et al., entitled "5'-Methylthioadenosine Nucleosidase is Implicated in Playing a Key Role in a Modified Futalosine Pathway for Menaquinone Biosynthesis in Campylobacter jejuni," J. Biol. Chem. 2011, vol. 286, p. 19392-19398.

* cited by examiner

TREATMENT OF HELICOBACTER PYLORI INFECTIONS

CROSS-REFERENCE TO RELATED APPLICATIONS

This application is a U.S. national stage entry under 35 U.S.C. § 371 of PCT International Patent Application No. PCT/US2013/053885, filed on Aug. 7, 2013, which claims the benefit of U.S. Provisional Application No. 61/680,334, filed on Aug. 7, 2012, and of U.S. Provisional Patent Application No. 61/806,476, filed on Mar. 29, 2013, the contents of all of which are hereby incorporated by reference.

STATEMENT OF GOVERNMENT SUPPORT

This invention was made with government support under grant numbers GM041916 and EB009998 awarded by the National Institutes of Health. The government has certain rights in the invention.

FIELD OF THE INVENTION

The invention relates to treating infections due to *Helicobacter pylori* (*H. pylori*) using inhibitors of *H. pylori* MTAN (5'-methylthioadenosine nucleosidase), in particular in subjects having a peptic ulcer.

BACKGROUND OF THE INVENTION

Throughout this application various publications are referred to in superscripts. Full citations for these references may be found at the end of the specification before the claims. The disclosures of these publications are hereby incorporated by reference in their entireties into the subject application to more fully describe the art to which the subject application pertains.

*H. pylori* is a gram-negative bacterium and lives microaerophilically in the gastric mucosa of its human host. It is related to 85 percent of gastric and 95 percent of duodenal ulcers[1]. Drug resistance is prevalent in clinical isolates of *H. pylori*. After less than thirty years of specific antibiotic treatment, it is increasingly difficult to eradicate *H. pylori* using a combination of two antibiotics with two weeks therapy. Antibiotics with new targets and mechanisms of action are needed to treat *H. pylori* infections.

Gram negative bacteria are dependent on menaquinone as electron transporters in respiration and have maintained biosynthetic pathways for these essential metabolites[3]. In contrast, humans lack the pathway of menaquinone synthesis, and targeting the menaquinone pathway may provide an anti-bacterial drug design approach. Recently, a menaquinone synthetic pathway has been proposed in *Campylobacter* and *Helicobacter* that differs from most bacteria[4,5]. In this pathway, 6-amino-6-deoxyfutalosine is synthesized by MqnA and cleaved at the N-ribosidic bond by a MTAN with specificity also extending to 5'-methylthioadenosine and adenosylhomocysteine as well as 6-amino-6-deoxyfutalosine. HpMTAN converts 6-amino-6-deoxyfutalosine to adenine and dehypoxanthine futalosine, the latter being used as the processor of menaquinone synthesis (FIG. 1A). The early reactions of this pathway do not exist in the normal bacterial flora of humans, making enzymes catalyzing these reactions appealing drug targets. HpMTAN is closely related to the 5'-methylthioadenosine/S-adenosylhomocysteine hydrolases (MTANs) found in other bacteria. The well-characterized MTANs are associated with quorum sensing and S-adenosylmethionine recycling in most species and are not essential for bacterial growth[6]. Transition state analogue inhibitors of picomolar to femtomolar affinity have been developed to interrupt bacterial functions associated with quorum sensing[6,7].

The present invention addresses the need for new compounds that selectively block the growth of *H. pylori*.

SUMMARY OF THE INVENTION

The invention provides methods of treating a *Helicobacter pylori* (*H. pylori*) infection in a subject comprising administering to the subject a compound of formula (I) in an amount effective to inhibit growth of *H. pylori*, wherein formula (I) is

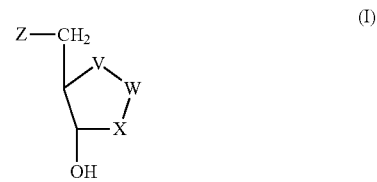

(I)

wherein V is $CH_2$ and W is NR, or V is NH and W is CHR; X is selected from $CH_2$ and CHOH in the R or S-configuration; Z is Q or SQ; where Q is C1-C7 alkyl, C4-C7 cycloalkyl, C4-C7 cycloalkylmethyl, aryl, heteroaryl or aralkyl, each of which is optionally substituted with one or more halogen or methyl groups, or Q is $CH_2=CH-(CH_2)_d-$ or $CH\equiv C-(CH_2)_d-$ where d is 0, 1, 2, 3, 4, 5, or 6, or Q is $R^1-(CH_2)_a-O-(CH_2)_b-$ where $R^1$ is H, OH, OMe, OEt, OPr, or $OCH_2CH_2OH$, a is 0, 1, 2, 3, 4, 5 or 6 and b is 1, 2, 3, 4, 5, 6, or 7 chosen such that the chain length of Z is no more than 8 C, O and S atoms, or Z is Q, where Q is $R^1-(CH_2)_e-S-CH_2-$ where $R^1$ is H, OH, OMe, OEt, OPr, or $OCH_2CH_2OH$, e is 2, 3, 4, 5 or 6 chosen such that the chain length of Q is no more than 8 C, O and S atoms; R is

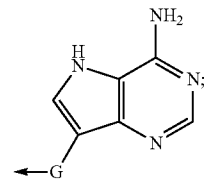

and G is $CH_2$ or G is absent; or a pharmaceutically acceptable salt thereof, or an ester thereof The invention further provides compounds having the structure of formula (II)

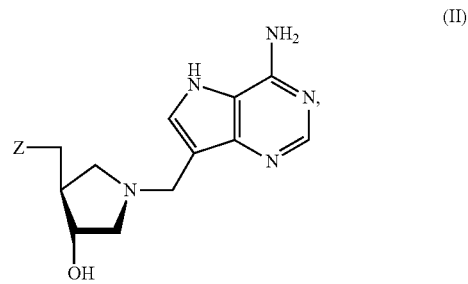

(II)

wherein Z is Q or SQ, and Q is C4-C7 cycloalkyl, heteroaryl, $R^1$—$(CH_2)_a$—, where $R^1$ is H and a is 5, 6, 7, or $R^1$ is OH, OMe, $CH_2$=CH—, or CH≡C—, OMe or $OCH_2CH_2OH$, and a is 2, 3, 4, 5, 6, or 7, chosen such that the chain length of Z is no more than 8 C, O and S atoms, or wherein Z is Q, and Q is R1-$(CH_2)_a$—, where $R^1$ is H and a is 4, or wherein Z is Q, and Q is $R^1$—$(CH_2)_e$—S—$CH_2$—, where $R^1$ is H, OH, OMe, OEt, OPr, or $OCH_2CH_2OH$, and e is 2, 3, or 4, or a pharmaceutically acceptable salt thereof, or an ester thereof.

DETAILED DESCRIPTION OF THE INVENTION

Figures 1A, 1B, 1C:
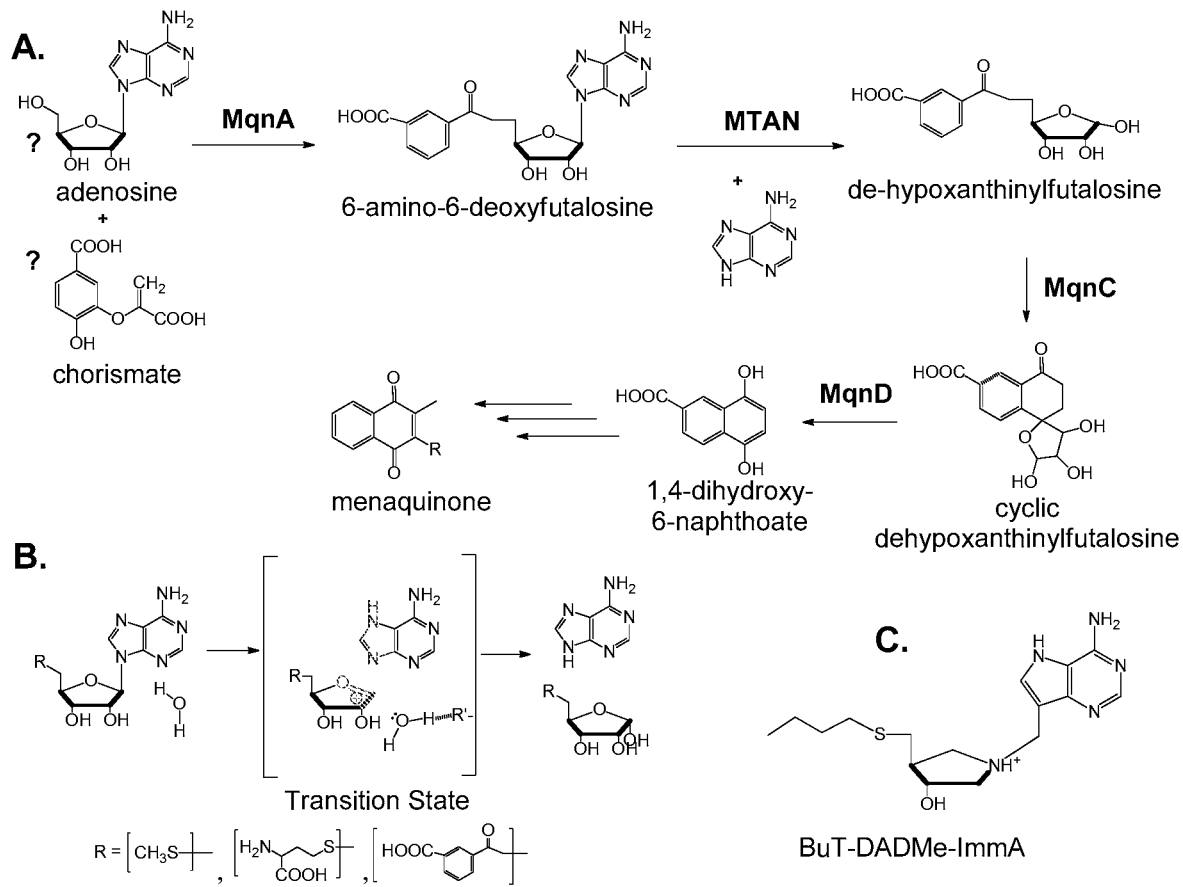
FIG. 1A-1C: Reactions catalyzed by MTANs, their proposed transition states and a transition state analogue inhibitor, BuT-DADMe-ImmA (30). A. Proposed early steps of the menaquinone pathway in *H. pylori*. The proposed substrates of MqnA reaction are labeled with question marks. B. Reaction catalyzed by HpMTAN and the proposed transition state. R' is a proton abstracting group leading to the formation of hydroxide from water after the transition state is passed. Candidates are Glu13 and Glu175 (FIG. 2). C. BuT-DADMe-ImmA (30).

The invention provides a method of treating a *Helicobacter pylori* (*H. pylori*) infection in a subject comprising administering to the subject a compound of formula (I) in an amount effective to inhibit growth of *H. pylori*, wherein formula (I) is

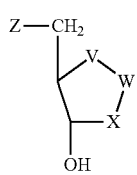
(I)

wherein V is $CH_2$ and W is NR, or V is NH and W is CHR;
X is selected from $CH_2$ and CHOH in the R or S-configuration;
Z is Q or SQ;
where Q is C1-C7 alkyl, C4-C7 cycloalkyl, C4-C7 cycloalkylmethyl, aryl, heteroaryl or aralkyl each of which is optionally substituted with one or more halogen or methyl groups, or
Q is $CH_2$=CH—$(CH_2)_d$— or CH≡C—$(CH_2)_d$— where d is 0, 1, 2, 3, 4, 5 or 6, or
Q is $R^1$—$(CH_2)_a$—O—$(CH_2)_b$— where $R^1$ is H, OH, OMe, OEt, OPr, or $OCH_2CH_2OH$, a is 0, 1, 2, 3, 4, 5 or 6 and b is 1, 2, 3, 4, 5, 6, or 7 chosen such that the chain length of Z is no more than 8 C, O and S atoms, or
Z is Q, where Q is $R^1$—$(CH_2)_e$—S—$CH_2$— where $R^1$ is H, OH, OMe, OEt, OPr, or $OCH_2CH_2OH$, e is 2, 3, 4, 5 or 6 chosen such that the chain length of Q is no more than 8 atoms;
R is

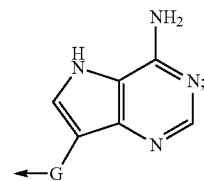

and
G is $CH_2$ or G is absent;
or a pharmaceutically acceptable salt thereof, or an ester thereof In one embodiment, the compound is a compound of formula (Ia), wherein formula (Ia) is

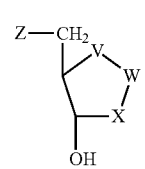
(Ia)

wherein V is $CH_2$ and W is NR, or V is NH and W is CHR;
X is selected from $CH_2$ and CHOH in the R or S-configuration;
Z is SQ or Q;
Q is C1-C5 alkyl, C4-C7 cycloalkyl, C4-C7 cycloalkylmethyl, aryl or aralkyl, each of which is optionally substituted with one or more halogen, hydroxy and/or methyl groups;
R is

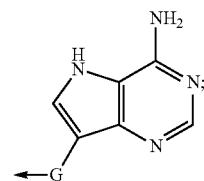

and

G is CH$_2$ or G is absent;

or a pharmaceutically acceptable salt thereof, or an ester thereof

Preferably V is CH$_2$, W is NR, G is CH$_2$, and X is CH$_2$; or V is NH, W is CHR, G is absent, and X is CHOH.

Z can be Q, CH$_2$Q or SQ. Preferred compounds include those where Z is SQ.

Q can be, for example, C1-C7 alkyl, e.g., C1-C5 alkyl; e.g., a methyl (Me), ethyl (Et), propyl (Pr), butyl or pentyl group. Q can be, for example, C4-C7 cycloalkyl, i.e., C4 cycloalkyl, C5 cycloalkyl, C6 cycloalkyl, or C7 cycloalkyl. Q can be, for example, aryl. The term "aryl" means an aromatic radical having 6 to 12 carbon atoms and includes heteroaromatic radicals. Preferred aryls include those having 6 carbon atoms. Q can also be, for example, C4-C7 cycloalkylmethyl or aralkyl e.g. a cyclohexylmethyl or benzyl group. Q can be substituted with, e.g., a methyl group, a hydroxy and/or a halogen, such as Cl, F, Br or I. Chlorine and fluorine are preferred halogens. The methyl group or halogen substitution can be at an ortho, meta or para position. Additional examples of Z and Q are illustrated herein.

Preferred compounds include those having the formula

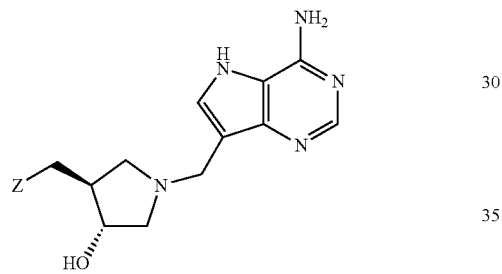

or the formula

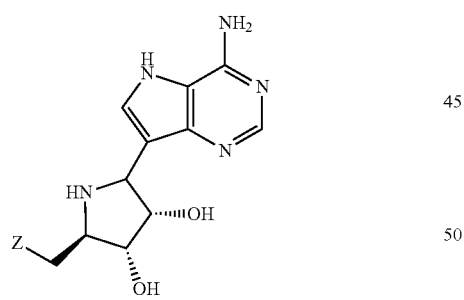

or a pharmaceutically acceptable salt thereof, or an ester thereof

Preferred compounds include those where Z is selected from the group consisting of

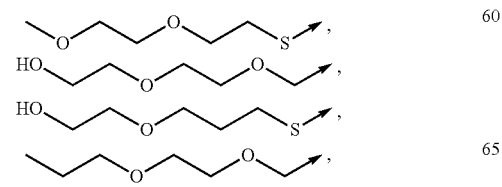

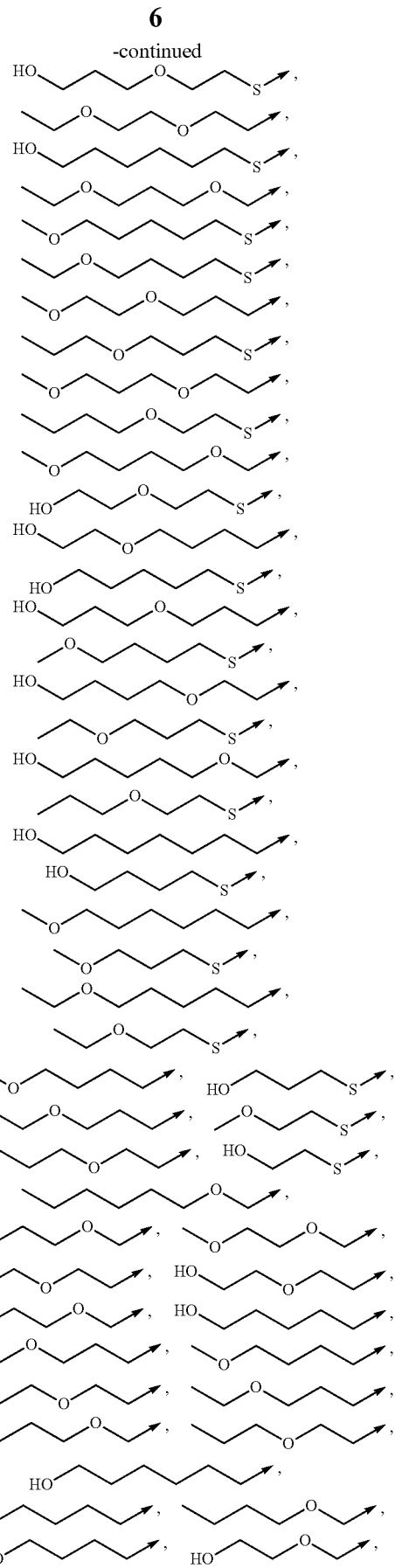

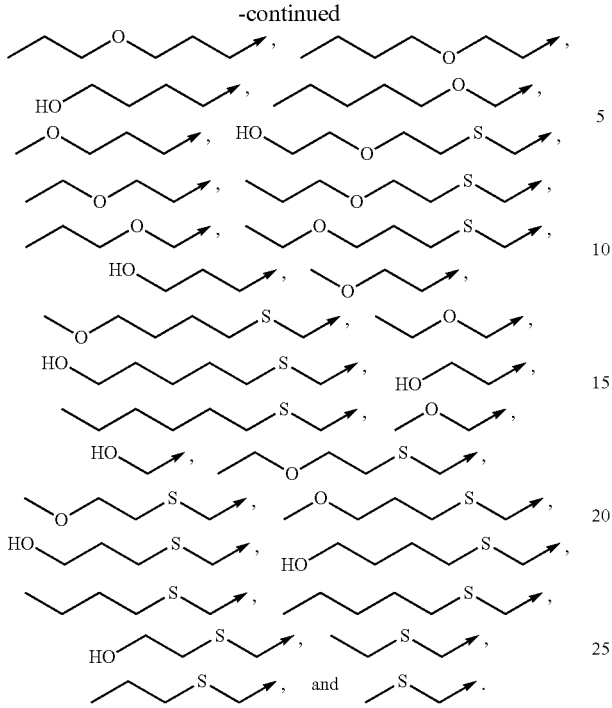
where the arrow indicates the point of attachment to the compound.
Preferred compounds include those selected from the group consisting of -continued
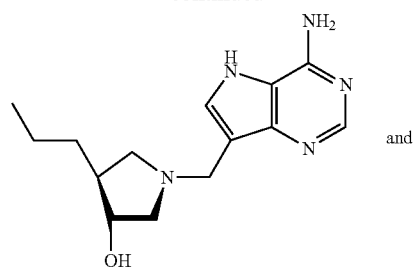
and
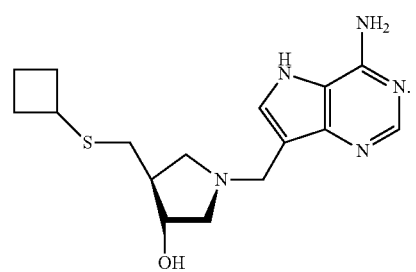
and those selected from the group consisting of
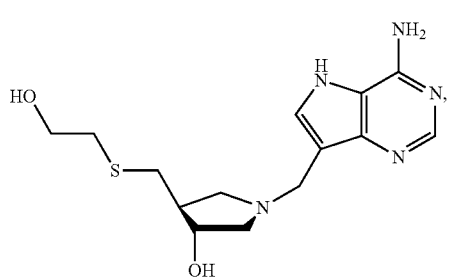
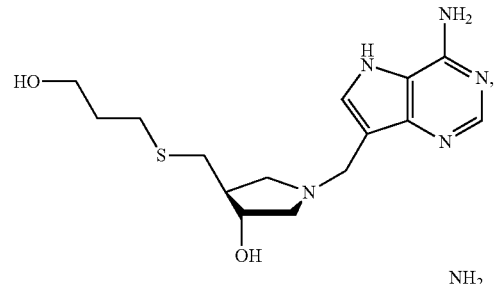
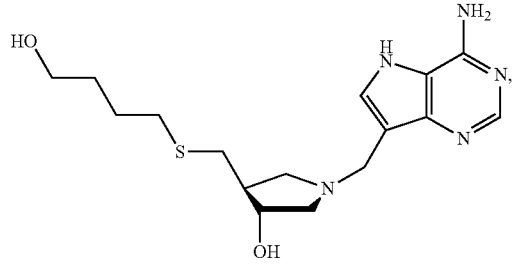
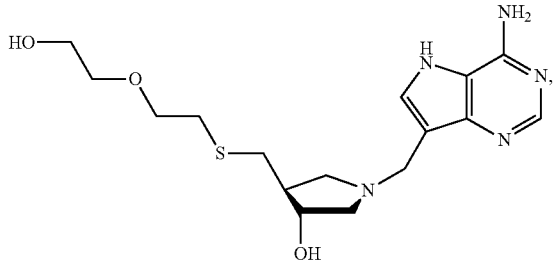
-continued
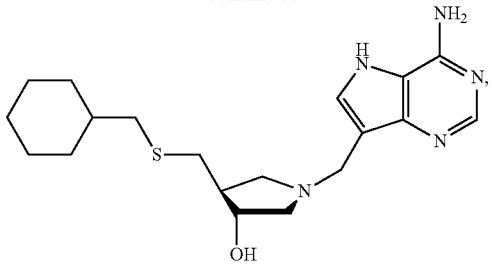
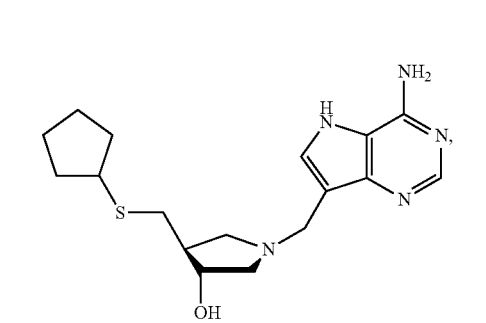
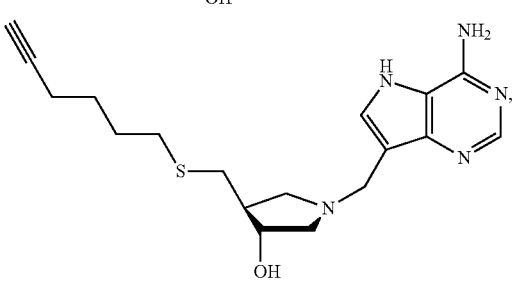
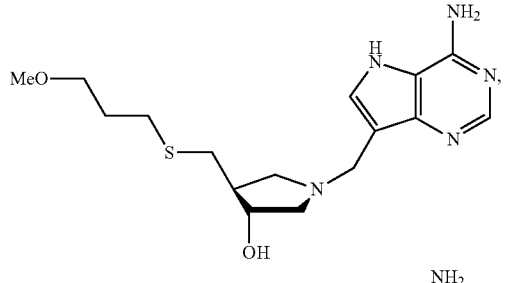
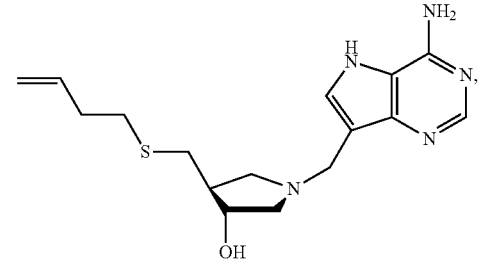
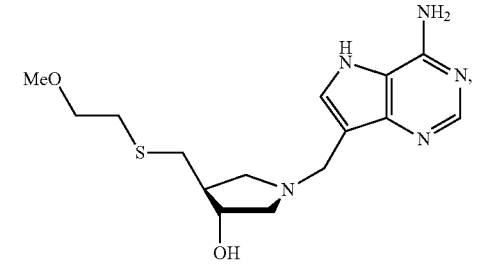

-continued
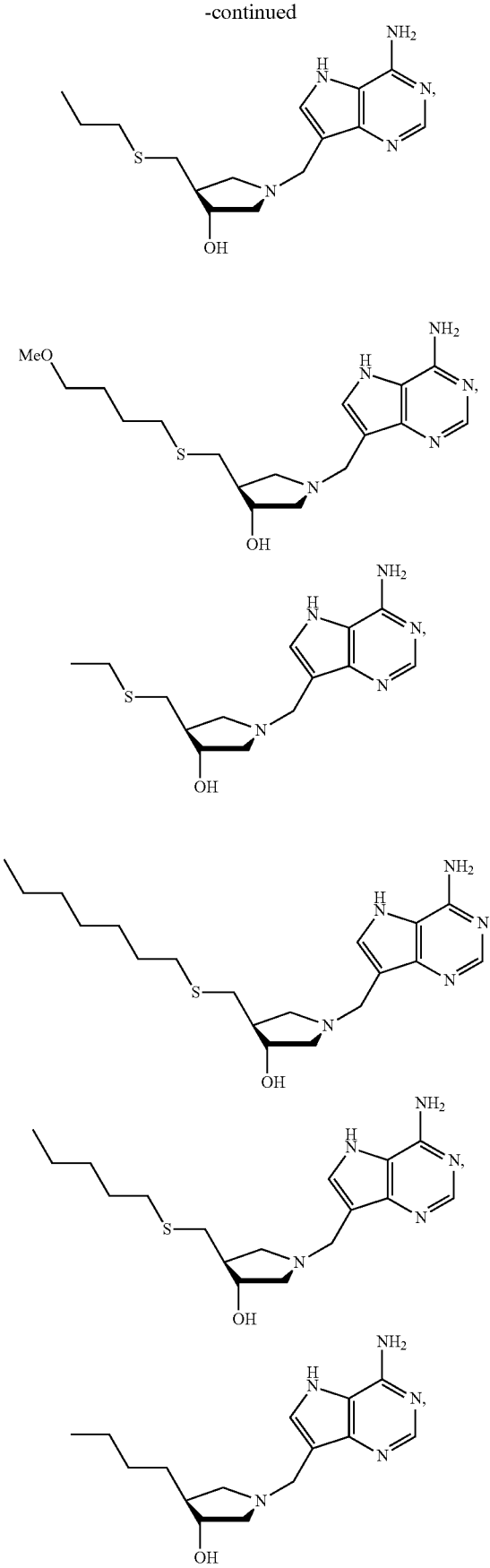
-continued
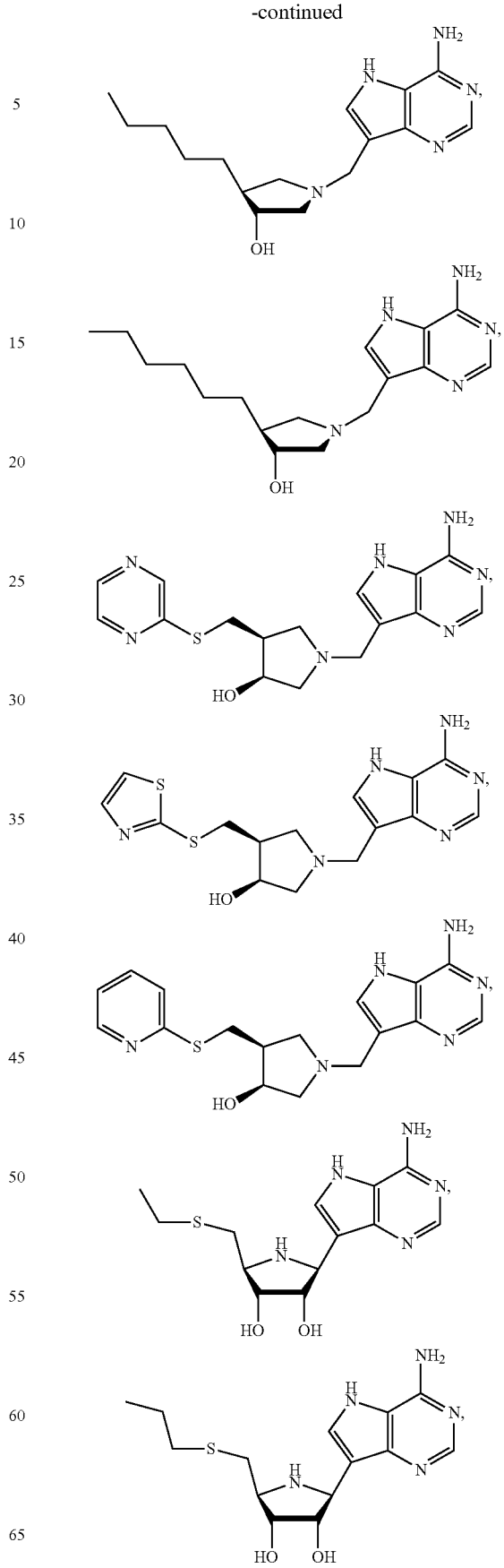

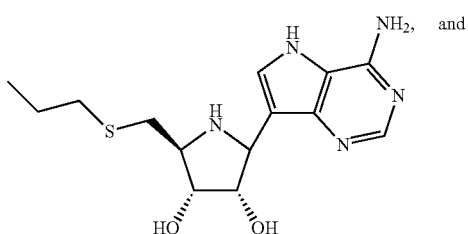
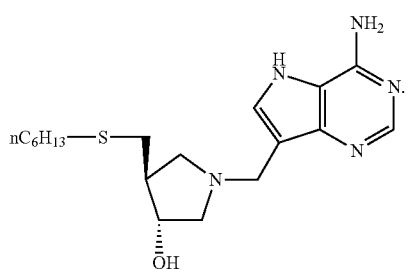
According, the invention provides a method of treating a *Helicobacter pylori* (*H. pylori*) infection in a subject comprising administering to the subject a compound in an amount effective to inhibit growth of *H. pylori*, wherein the compound is selected from the group consisting of:
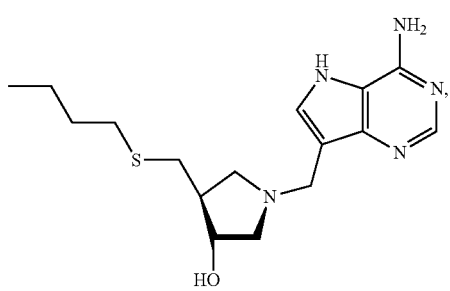
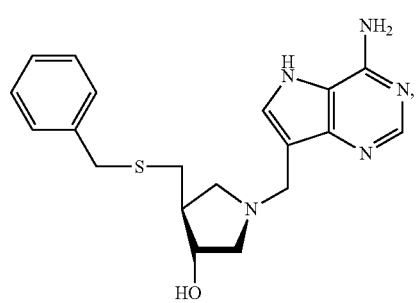
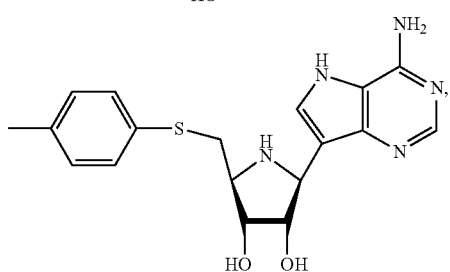
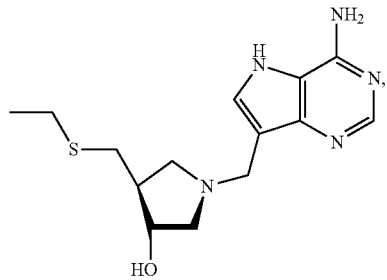
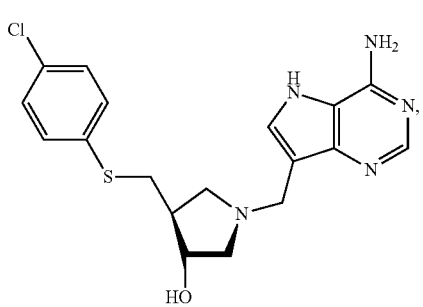
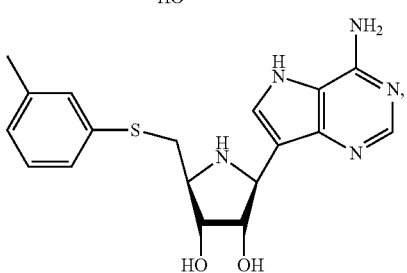
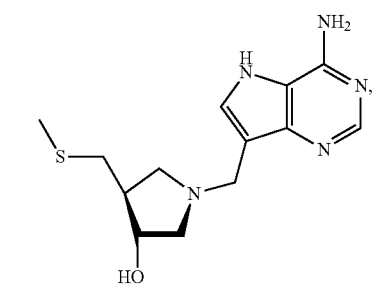
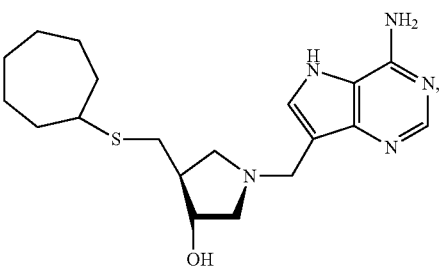
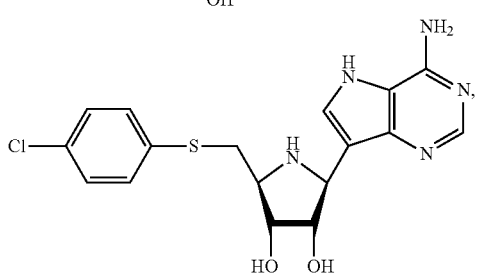

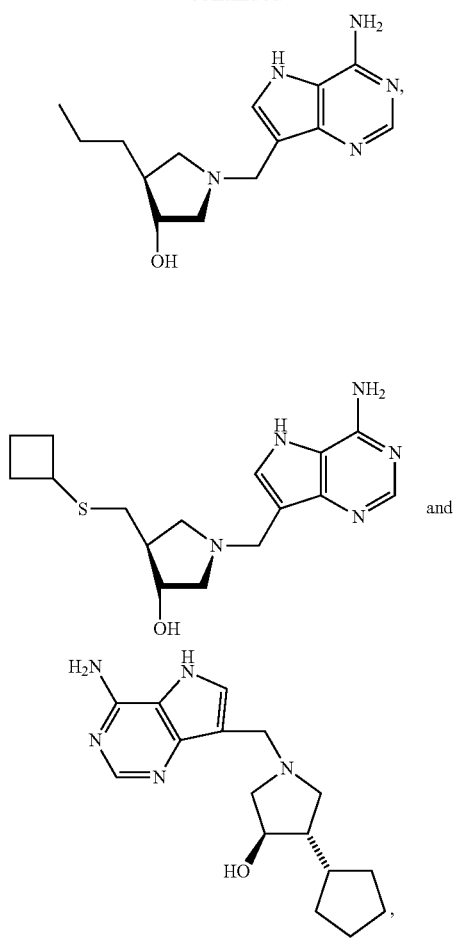
or a pharmaceutically acceptable salt thereof, or an ester thereof, and from the group consisting of
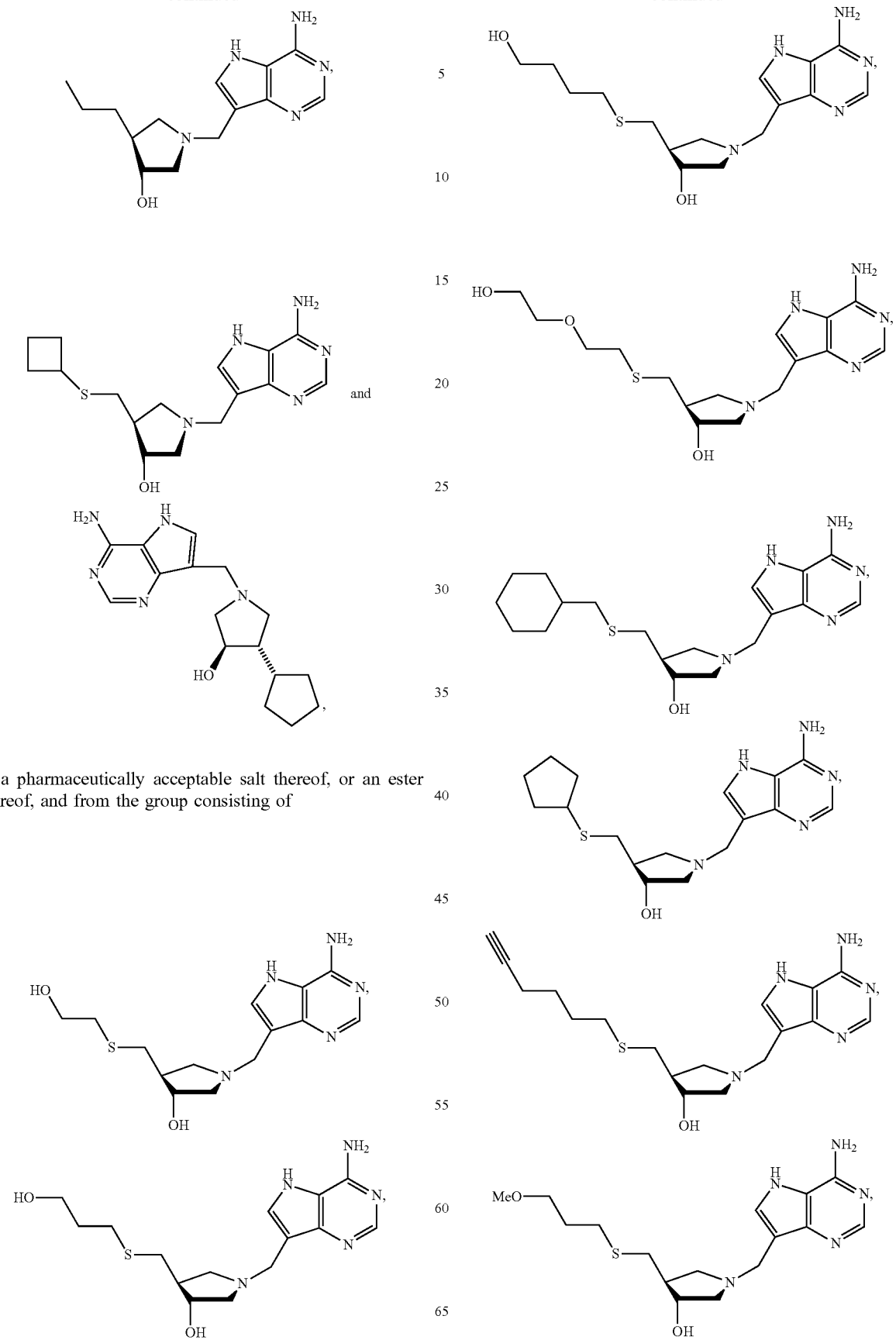

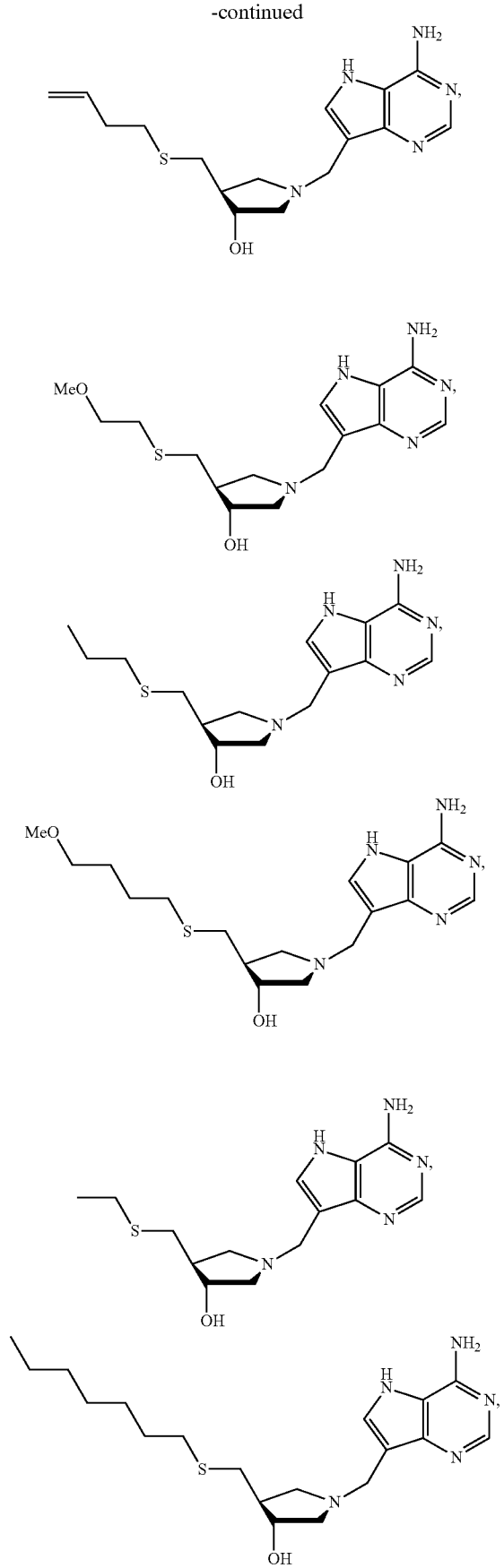
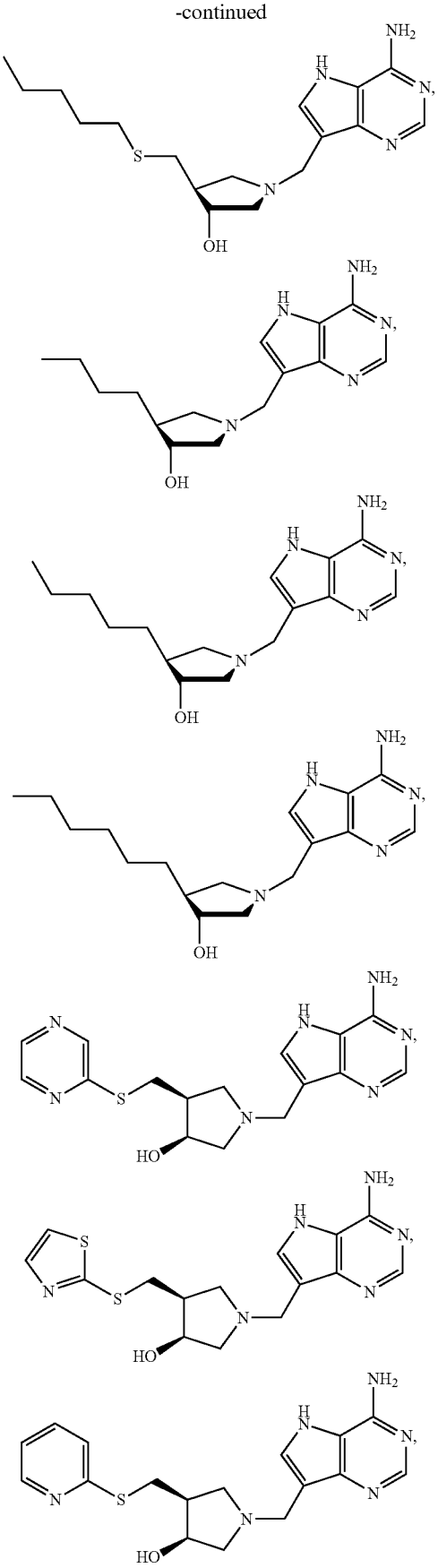

-continued

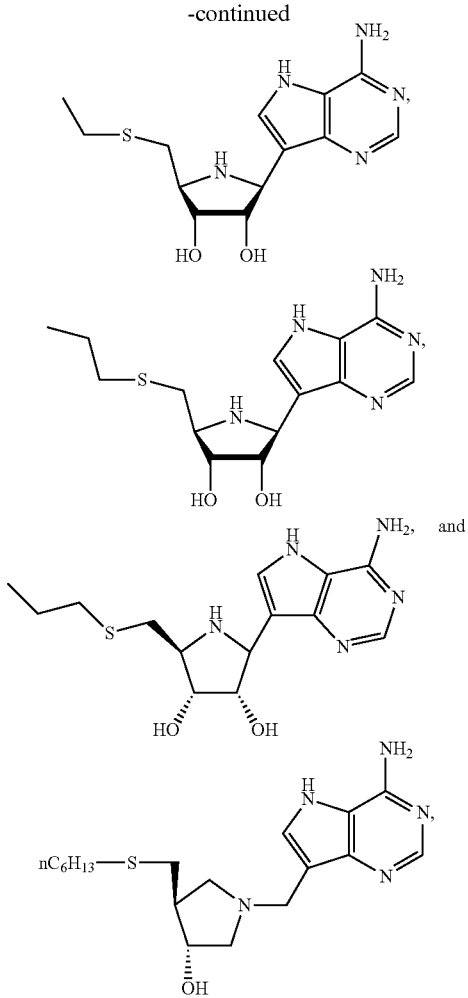

or a pharmaceutically acceptable salt thereof, or an ester thereof

Preferred compounds include

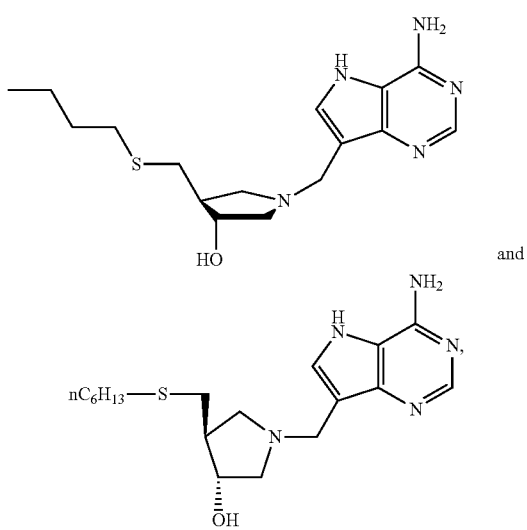

or a pharmaceutically acceptable salt thereof, or an ester thereof

The term "pharmaceutically acceptable salts" includes non-toxic salts derived from inorganic or organic acids, including, for example, the following acid salts: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, p-toluenesulfonate, salicylate, succinate, sulfate, tartrate, thiocyanate, and undecanoate.

Preferably, the compound is administered in an amount that is effective to inhibit H. pylori 5'-methylthioadenosine nucleosidase (MTAN).

In one embodiment of the method using a compound where V is $CH_2$ and W is NR, X is $CH_2$, G is $CH_2$, and Z is SQ, then Q is not methyl, ethyl, benzyl or para-chlorophenyl.

Preferably, the compound inhibits growth of H. pylori but does not inhibit the growth of one or more bacterium selected from the group consisting of E. coli, V. cholerae, S. aureus, K. pneumoniae, S. flexneri, S. enterica and P. aeruginosa. More preferably, the compound does not inhibit the growth of all of E. coli, V. cholerae, S. aureus, K. pneumoniae, S. flexneri, S. enterica and P. aeruginosa. Preferably, the compound is more effective in inhibiting growth of H. pylori than is amoxicillin, metronidazole or tetracyclin.

Preferably, the subject has a peptic ulcer, such as a gastric ulcer or a duodenal ulcer.

Preferably, the compound is administered orally. For oral administration, the compound can be formulated into solid or liquid preparations, for example tablets, capsules, powders, solutions, suspensions and dispersions. The compound can be formulated with agents such as, e.g., lactose, sucrose, corn starch, gelatin, potato starch, alginic acid and/or magnesium stearate.

The compound can also be administered to a subject by other routes known in the art, such as, e.g., parenterally, by inhalation, topically, rectally, nasally, buccally or via an implanted reservoir. The compound can be administered by means of sustained release.

The invention further provides for the use a compound that inhibits Helicobacter pylori (H. pylori) MTAN for the preparation of a medicament for treating a H. pylori infection. The invention still further provides a compound that inhibits Helicobacter pylori (H. pylori) MTAN for use for treating a H. pylori infection.

The invention further provides for the use a compound that inhibits Helicobacter pylori (H. pylori) MTAN for the preparation of a medicament for treating a peptic ulcer. The invention still further provides a compound that inhibits Helicobacter pylori (H. pylori) MTAN for use for treating a peptic ulcer.

The present methods can also be applied to treating infections due to other Helicobacter species and to Campylobacter species, such as C. jejuni.

The invention further provides a compound having the structure of formula (II)

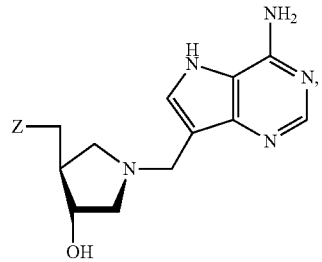
(II)

wherein Z is Q or SQ, and Q is C4-C7 cycloalkyl, heteroaryl, $R^1$—$(CH_2)_a$—, where $R^1$ is H and a is 5, 6, or 7, or $R^1$ is OH, OMe, $CH_2$=CH—, CH≡C—, OMe or $OCH_2CH_2OH$, and a is 2, 3, 4, 5, 6, or 7, or wherein Z is Q, and Q is $R^1$—$(CH_2)_a$—, where $R^1$ is H and a is 4, or wherein Z is Q, and Q is $R^1$—$(CH_2)_e$—S—$CH_2$—, where $R^1$ is H, OH, OMe, OEt, OPr, or $OCH_2CH_2OH$, and e is 2, 3, or 4, or a pharmaceutically acceptable salt thereof, or an ester thereof.

Preferred compounds include those having the structure

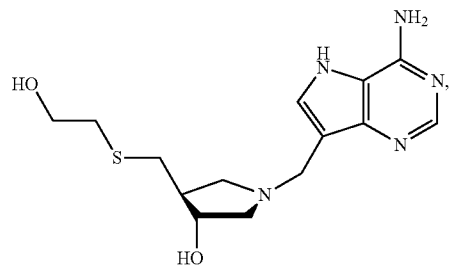

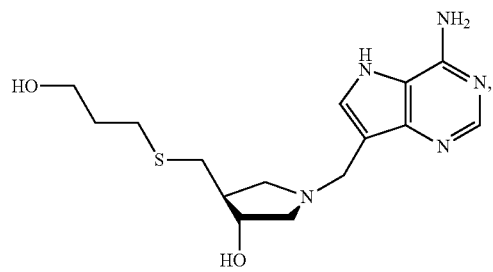

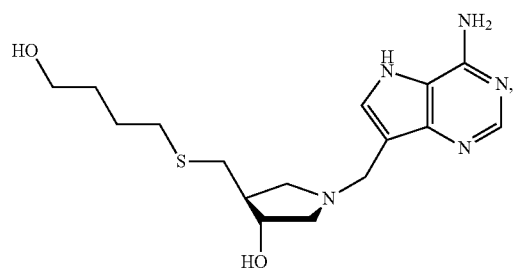

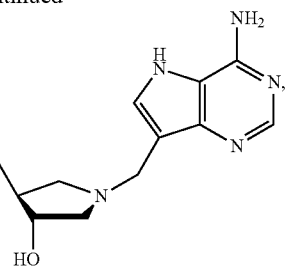

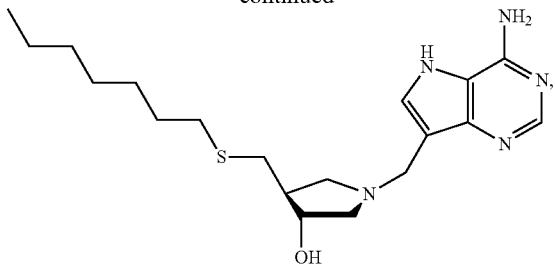
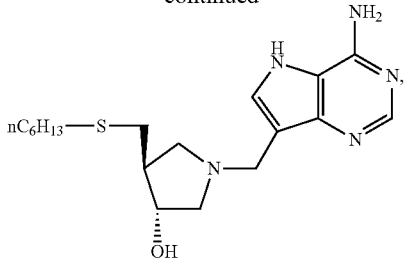
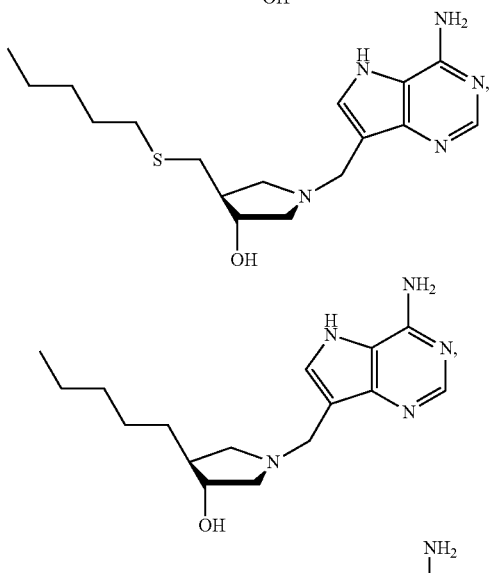
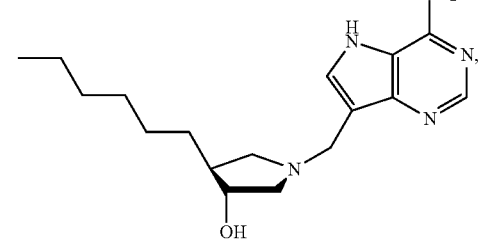
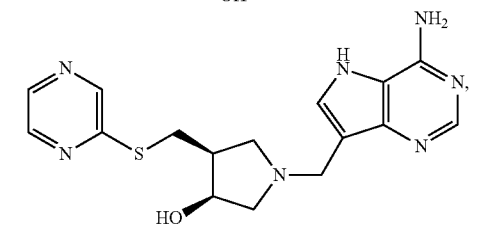
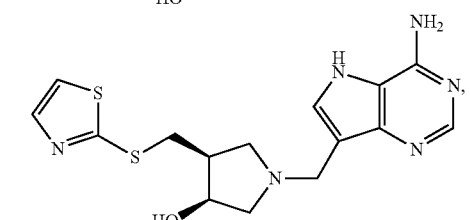
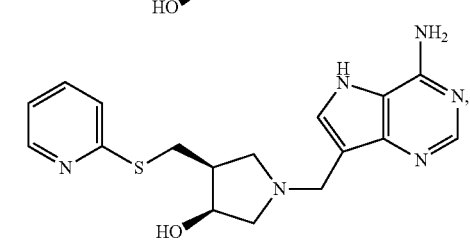

or a pharmaceutically acceptable salt thereof, or an ester thereof

The invention further provides a pharmaceutical composition comprising any of the compounds disclosed herein and a pharmaceutically acceptable carrier. As used herein, a "pharmaceutically acceptable carrier" is (i) compatible with the other ingredients of the composition without rendering the composition unsuitable for its intended purpose, and (ii) suitable for use with subjects as provided herein without undue adverse side effects (such as toxicity, irritation, and allergic response). Side effects are "undue" when their risk outweighs the benefit provided by the composition. Non-limiting examples of pharmaceutically acceptable carriers include any of the standard pharmaceutical carriers such as phosphate buffered saline solutions, water, and emulsions such as oil/water emulsions and microemulsions.

This invention will be better understood from the Experimental Details that follow. However, one skilled in the art will readily appreciate that the specific methods and results discussed are merely illustrative of the invention as described more fully in the claims that follow thereafter.

EXPERIMENTAL DETAILS

Introduction

Transition state features of several bacterial MTANs are known to have ribocationic character with minimal participation of the attacking water nucleophile and a neutral adenine leaving group[8-10]. In the present study, it was assumed that the transition state of HpMTAN would be similar based on its homology to other MTANs (FIG. 1B)[4]. Transition state analogues are known to bind tightly to their cognate enzymes[11,12] by converting the dynamic protein motion involved in catalysis to a more stable thermodynamic state[13].

Materials and Methods

Materials.

*H. pylori* (J99 and 43504), *K. pneumoniae*, *S. flexneri*, *S. enterica*, *S. aureus* and *P. aeruginosa* were purchased from the American Type Culture Collection. Defibrinated horse blood (DHB) was from Hemostat Laboratories (Dixon, Calif.). Tryptic soy agar (TSA) was purchased from Becton Dickinson and Company (Sparks, Md.). MacConkey agar was from Oxoid LTD. (Basingstoke, Hampshire, England). Xanthine oxidase and 5'-methylthioadenosine were purchased from Sigma-Aldrich (St Louis, Mo.). The rest of the materials were purchased with the highest purity available.

The synthesis of BuT-DADMe-ImmA (30) ((3R,4S)-4-(1-butylthiomethyl)-1-[(9-deaza-adenin-9-yl)-methyl]-3-hydroxypyrrolidine) has been previously described with the final step consisting of a 3 component Mannich reaction, between (3R,4S)-4-butylthiomethyl-3-hydroxypyrrolidine hydrochloride, 9-deazaadenine and formaldehyde to afford the compound[21]. The structure and purity (>95%) of BuT-DADMe-ImmA was confirmed by NMR, HPLC and microanalysis. Synthesis of 6-amino-6-deoxyfutalosine was accomplished as previously reported[22].

HpMTAN Purification.

The purification procedure of HpMTAN was described previously[10]. Briefly, BL21 (DE3) cells harboring a plasmid encoding HpMTAN with an N-terminal His6-tag were grown to an optical density of 0.7 measured at 595 nm and IPTG was introduced to a final concentration of 0.5 mM. After another 15 h at 22° C., cells were collected by centrifugation. The pellet was suspended and later disrupted by pressure cell and sonication. The soluble portion was applied to a Ni-NTA column and HpMTAN was eluted with an imidazole concentration gradient of 200 to 500 mM. The protein was desalted using a Superdex G15 gel-filtration column then equilibrated and concentrated in 10 mM Hepes, 30 mM KCl, pH 7.6. The purity was confirmed by SDS-PAGE.

$K_i$ Determination.

Kinetics of HpMTAN were determined using a direct assay involving absorbance decrease at 274 nm continuously as a consequence of formation of free adenine from 5'-methylthioadenosine. The $K_i$ and $K_i^*$ values of BuT-DADMe-ImmA (30) were determined using coupled assays, in which xanthine oxidase was used as the coupling enzyme and absorbance increase was followed at 292 nm as the product adenine is converted to 2,8-dihydroxyadenine. Both assays have been previously described Bacterial Growth.

H. pylori were grown for 72 hours under microaerophilic condition (5% $O_2$, 10% $CO_2$ and 85% $N_2$) at 37° C. on tryptic soy agar with 5% horse blood. To determine the MIC values, the test substance was added to the gel solution right before pouring. To compare the zones of inhibition, specific antibiotics were added to the center of disc after spreading H. pylori, and then H. pylori was allowed to grow for 72 hours under microaerophilic condition at 37° C.

At the desired concentration of the test substance BuT-DADMe-ImmA (30), K pneumoniae, S. flexneri and S. enterica were grown on MacConkey agar at 37° C. for 24 hours, and S. aureus and P. aeruginosa were grown on LB agar at 37° C. for 24 hours.

Protein Crystallization and Data Collection.

Prior to crystallization, BuT-DADMe-ImmA (30) was added into 15 mg/ml HpMTAN solution to reach a concentration of 1 mM. The HpMTAN crystals grew from 0.1 M Tris, pH 8.5, 1.2 M tri-sodium citrate solution in 3-5 days at room temperature using the sitting-drop vapor diffusion method. Crystals of the HpMTAN and BuT-DADMe-ImmA complex were transferred into a fresh drop of the crystallization solution containing 10-15% glycerol and rapidly frozen in liquid nitrogen. X-ray diffraction data was collected at Beamline X29A at Brookhaven National Laboratory. Datasets were processed with the HKL3000 program suite[23] and the processing statistics are shown in Table 1.

Structure Determination and Refinement.

The crystal structure of HpMTAN with BuT-DADMe-ImmA (30) was determined by molecular replacement using MOLREP[24] of CCP4 program suite[25,26] with structure of N. meningitidis MTAN (PDB code 3EEI) as the search model. The model was first rebuilt in COOT[27] and refined in REFMAC5[28]. BuT-DADMe-ImmA was added last using $F_o$-Fc map at 3σ. The quality of the structure was checked by PROCHECK[29] and MOLPROBITY[30,31]. The refinement and geometry statistics are provided in Table 1. The coordinate and structure factor files have been deposited into the Protein Data Bank as entries 4FFS and RCSB072846, respectively.

Synthesis of DADMe-Immucillins

In general the desired DADMe-Immucillins of general structure 6 were synthesised via the readily available alcohols 1 and 2 [Clinch, et al.[37]] (Scheme 1). Sulfonylation of was achieved under standard conditions with methanesulfonyl chloride to afford mesylates 3 or 4. Following this, two equivalents of the appropriate mercaptan was treated with NaH in DMF and the sulfur nucleophile thus formed was allowed to react preferentially with the 3 or 4 to afford the desired carbamates which gave the desired amines of general structure 5 in good yields following acid deprotection then chromatographic purification on silica with ammonia added to the eluent. The free bases 5 then formed one part of a three component Mannich reaction along with 9-deazaadenine (9-DAA) and formaldehyde to yield the desired DADMe-Immucillins 6 in moderate to good yields following chromatography.

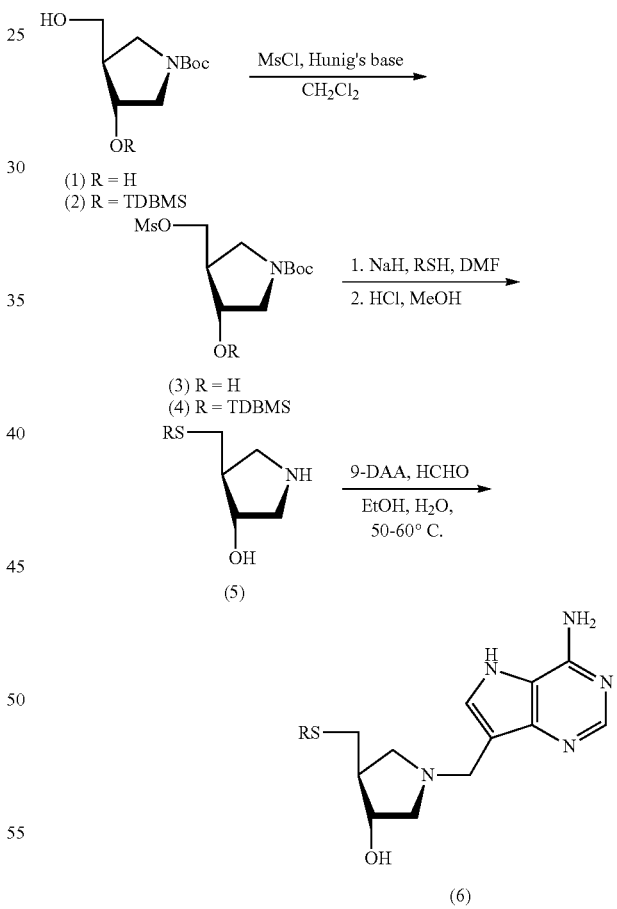

Scheme 1.

The one carbon homologated DADMe-Immucillins of general structure 9 were formed via the carbamate 2 which was converted to mesylate 7 in 4 steps (Scheme 2). These steps involved a Dess-Martin periodinane (DMP) oxidation, followed by a Wittig reaction, hydroboration of the alkene thus formed and finally mesylation under standard conditions to afford mesylate 7. The mesylate group was then able to be displaced by either a sulfur or oxygen nucleophile.

Thus, two equivalents of the appropriate mercaptan or alcohol was treated with NaH in DMF and the anion thus formed was allowed to react with the mesylate 7 to afford the desired carbamates which gave the desired amines of general structure 8 in good yields following deprotection either through treatment with HCl or a two-step process using TFA and TBAF then chromatographic purification on silica with ammonia added to the eluent. The resulting amines 8 then formed one part of a three component Mannich reaction along with 9-deazaadenine (9-DAA) and formaldehyde to yield the desired chain extended DADMe-Immucillins of general structure 9 in moderate to good yields following chromatography.

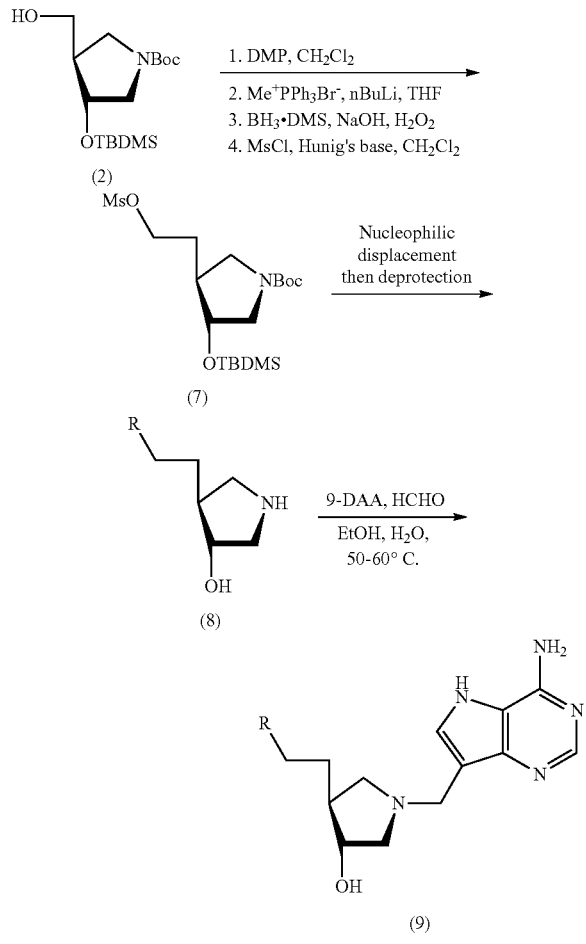

All reactions were performed under an argon atmosphere. Organic solutions were dried over anhydrous MgSO$_4$ and the solvents were evaporated under reduced pressure. Anhydrous and chromatography solvents were obtained commercially and used without any further purification. Thin layer chromatography (TLC) was performed on aluminum sheets coated with 60 F254 silica gel. Organic compounds were visualized under UV light and/or a dip of Ehrlich's solution or ammonium molybdate (5 mass %) and cerium(IV) sulfate.4 H$_2$O (0.2 mass %) in aq. H$_2$SO$_4$ (2 M). Flash chromatography was performed on silica gel (40-63 µm). $^1$H and $^{13}$C NMR spectra were measured in CDCl$_3$, CD$_3$OD, D$_2$O, or CD$_6$SO. Assignments of $^1$H and $^{13}$C resonances were based on 2D (1H-1H DQF-COSY, 1H-13C HSQC) and DEPT experiments. Abbreviations used: s, singlet; d, doublet; t, triplet; q, quartet; bs, broad singlet; bt, broad triplet; dd, doublet of doublets; ddd, doublet of doublets of doublets; dt, doublet of triplets. High resolution electrospray mass spectra (ESI-HRMS) were recorded on a Q-TOF Tandem Mass Spectrometer.

(4S)-4-(((2-Hydroxyethyl)thio)methyl)pyrrolidin-3-ol (5, R=CH$_2$CH$_2$OH). Methanesulfonyl chloride (0.175 ml, 2.262 mmol) was added to a solution of alcohol 1 (500 mg, 1.508 mmol) and Hunig's base (0.788 ml, 4.52 mmol) in dichloromethane (10 mL) and the mixture stirred for 1 h at room temperature. On completion the reaction was diluted with chloroform and washed with water and saturated NaHCO$_3$, dried (MgSO$_4$) and concentrated in vacuo. The crude mesylate 2 (620 mg, 100%) was committed to the next step without further purification or characterisation. Sodium hydride (121 mg, 3.02 mmol, 60 wt % in oil, 2 eq) was added to a solution of 2-mercaptoethanol (212 µL, 3.02 mmol, 2 eq) in dimethylformamide (5 mL) and the resulting suspension stirred for 10 minutes. After this time a solution of crude mesylate 2 (620 mg, 1.5 mmol) in dimethylformamide (5 mL) was added and the resulting mixture left to stir for 30 minutes at room temperature. The mixture was diluted with toluene and washed with water and brine, dried and concentrated in vacuo. The residue was purified on silica gel (eluent 30%=>50% ethyl acetate in petroleum ether) to afford the desired carbamate (425 mg, 72% for 2 steps) as an oil which was committed to the next step without characterization. cHCl (2 mL) was added to a solution of carbamate (425 mg, 0.92 mmol) in methanol (4 mL) and the mixture concentrated in vacuo. The resulting residue was dissolved in additional cHCl (2 mL) and concentrated in vacuo and the residue partitioned between water and chloroform. The aqueous layer was washed with further chloroform and then concentrated in vacuo. The residue was purified and converted to the free base by chromatography on silica gel (eluent 20=>25% [7N NH$_3$ in MeOH] in CHCl$_3$) to afford the title compound 5 (R=CH$_2$CH$_2$OH) (199 mg, 73%) as a syrup. $^1$H NMR (500 MHz, MeOD): δ=4.09 (dt, J=5.5, 3.5 Hz, 1H), 3.69 (t, J=6.8 Hz, 2H), 3.23 (dd, J=11.6, 7.6 Hz, 1H), 3.01 (dd, J=12.0, 5.5 Hz, 1H), 2.76 (dd, J=12.0, 3.5 Hz 1H), 2.73-2.61 (m, 4H), 2.50 (dd, J=12.8, 8.6 Hz, 1H), and 2.19-2.12 ppm (m, 1H). $^{13}$C NMR (500 MHz, MeOD): δ=77.7, 62.5, 54.8, 51.5, 49.3, 35.6, and 35.4 ppm. ESI-HRMS for C$_7$H$_{16}$NO$_2$S [MH]$^+$ calcd 178.0902. found 178.0900.

(4S)-4-(((3-Hydroxypropyl)thio)methyl)pyrrolidin-3-ol (5, R=CH$_2$CH$_2$CH$_2$OH). Sodium hydride (137 mg, 3.42 mmol, 60 wt % in oil, 2 eq) was added to a solution of 3-mercapto-1-propanol (460 µL, 3.02 mmol, 3 eq) in dimethylformamide (5 mL) and the resulting suspension stirred for 10 minutes. After this time a solution of crude mesylate 2 (700 mg, 1.7 mmol) in dimethylformamide (5 mL) was added and the resulting mixture left to stir for 30 minutes at room temperature. The mixture was diluted with toluene and washed with water and brine, dried and concentrated in vacuo. The residue was purified on silica gel (eluent 40% ethyl acetate in petroleum ether) to afford the desired carbamate (361 mg, 52% for 2 steps) as a colourless syrup which was committed to the next step without characterisation. cHCl (2 mL) was added to a solution of carbamate (361 mg, 0.89 mmol) in methanol (4 mL) and the mixture concentrated in vacuo. The resulting residue was dissolved in additional cHCl (2 mL) and concentrated in vacuo and the residue partitioned between water and chloroform. The aqueous layer was washed with further chloroform and then concentrated in vacuo. The residue was purified and converted to the free base by chromatography on silica gel (eluent 20% [7N $NH_3$ in MeOH] in $CHCl_3$) to afford the title compound 5 (R=$CH_2CH_2CH_2OH$) (135 mg, 79%) as a colourless syrup. $^1$H NMR (500 MHz, MeOD): δ=4.05 (dt, J=5.5, 3.5 Hz, 1H), 3.64 (t, J=6.3 Hz, 2H), 3.22 (dd, J=11.5, 7.5 Hz, 1H), 3.00 (dd, J=12.1, 5.6 Hz, 1H), 2.75 (dd, J=12.0, 3.5 Hz 1H), 2.67 (dd, J=12.8, 6.6 Hz 1H), 2.64-2.60 (m, 3H), 2.46 (dd, J=12.8, 8.7 Hz, 1H), 2.19-2.12, and 1.82-1.76 ppm (m, 2H). $^{13}$C NMR (500 MHz, MeOD): δ=77.8, 61.5, 54.9, 51.5, 49.2, 35.2, 33.6, and 29.6 ppm. ESI-HRMS for $C_8H_{18}NO_2S$ [MH]$^+$ calcd 192.1058. found 192.1061.

(4S)-4-(((4-Hydroxybutyl)thio)methyl)pyrrolidin-3-ol [5, R=—$(CH_2)_4OH$]

Sodium hydride (137 mg, 3.42 mmol, 60 wt % in oil, 2 eq) was added to a solution of 4-mercapto-1-butanol (556 μL, 3.02 mmol, 3 eq) in dimethylformamide (5 mL) and the resulting suspension stirred for 10 minutes. After this time a solution of crude mesylate 2 (700 mg, 1.7 mmol) in dimethylformamide (5 mL) was added and the resulting mixture left to stir for 30 minutes at room temperature. The mixture was diluted with toluene and washed with water and brine, dried and concentrated in vacuo. The residue was purified on silica gel (eluent 40% ethyl acetate in petroleum ether) to afford the desired carbamate (458 mg, 64% for 2 steps) as a colourless syrup which was committed to the next step without characterisation. cHCl (2 mL) was added to a solution of carbamate (458 mg, 0.89 mmol) in methanol (4 mL) and the mixture concentrated in vacuo. The resulting residue was dissolved in additional cHCl (2 ml) and concentrated in vacuo and the residue partitioned between water and chloroform. The aqueous layer was washed with further chloroform and then concentrated in vacuo. The residue was purified and converted to the free base by chromatography on silica gel (eluent 20% [7N $NH_3$ in MeOH] in $CHCl_3$) to afford the title compound 5 [R=—$(CH_2)_4OH$] (185 mg, 82%) as a colourless syrup. $^1$H NMR (500 MHz, MeOD): δ=4.04 (dt, J=5.5, 3.5 Hz, 1H), 3.56 (t, J=6.2 Hz, 2H), 3.22 (dd, J=11.5, 7.5 Hz, 1H), 3.00 (dd, J=12.0, 5.5 Hz, 1H), 2.75 (dd, J=12.0, 3.4 Hz 1H), 2.67 (dd, J=12.8, 6.6 Hz 1H), 2.63 (dd, J=11.7, 6.0 Hz 1H), 2.57 (t, J=7.0 Hz, 2H), 2.45 (dd, J=12.8, 8.7 Hz, 1H), 2.18-2.12 (m, 1H), 1.69-1.59 (m, 4H) and ppm. $^{13}$C NMR (500 MHz, MeOD): δ=77.8, 62.5, 54.9, 51.5, 49.2, 35.1, 33.0, 32.8, and 27.2 ppm. ESI-HRMS for $C_9H_{20}NO_2S$ [MH]$^+$ calcd 206.1215. found 206.1214.

(4S)-4-(((2-(2-Hydroxyethoxyl)ethyl)thio)methyl) pyrrolidin-3-ol (5, R=$CH_2CH_2OCH_2CH_2OH$). Sodium hydride (121 mg, 3.02 mmol, 60 wt % in oil) was added to a solution of 2-(2-mercaptoethoxyl)ethanol (369 mg, 3.02 mmol, 2 eq) in dimethylformamide (5 mL) and the resulting suspension stirred for 10 minutes. After this time a solution of crude mesylate 2 (620 mg, 1.5 mmol) in dimethylformamide (5 mL) was added and the resulting mixture left to stir for 30 minutes at room temperature. The mixture was diluted with toluene and washed with water and brine, dried and concentrated in vacuo. The residue was purified on silica gel (eluent 30%=>50% ethyl acetate in petroleum ether) to afford the desired carbamate (360 mg, 61% for 2 steps) as an oil which was committed to the next step without characterization. cHCl (2 mL) was added to a solution of carbamate (360 mg, 0.92 mmol) in methanol (4 mL) and the mixture concentrated in vacuo. The resulting residue was dissolved in additional cHCl (2 mL) and concentrated in vacuo and the residue partitioned between water and chloroform. The aqueous layer was washed with further chloroform and then concentrated in vacuo. The residue was purified and converted to the free base by chromatography on silica gel (eluent 20=>25% [7N $NH_3$ in MeOH] in $CHCl_3$) to afford the title compound 5 (R=$CH_2CH_2OCH_2CH_2OH$) (151 mg, 74%) as a syrup. $^1$H NMR (500 MHz, MeOD): δ=4.04 (dt, J=5.5, 3.5 Hz, 1H), 3.68-3.64 (m, 3H), 3.56-3.53 (m, 2H), 3.22 (dd, J=11.5, 7.5 Hz, 1H), 3.01 (dd, J=12.0, 5.5 Hz, 1H), 2.78-2.71 (m, 3H), 2.64 (dd, J=11.5, 5.8 Hz, 1H), 2.52 (dd, J=12.8, 8.7 Hz, 1H), and 2.21-2.13 ppm (m, 1H). $^{13}$C NMR (500 MHz, MeOD): δ=77.7, 73.4, 72.1, 62.3, 54.8, 51.5, 49.2, 35.6, and 32.6 ppm. ESI-HRMS for $C_9H_{20}NO_3S$ [MH]$^+$ calcd 222.1164. found 222.1160.

(4S)-1-((4-amino-5H-pyrrolo[3,2-d]pyrimidin-7-yl) methyl)-4-(((2-hydroxyethyl)thio)methyl)pyrrolidin-3-ol (10)

Amine 5 (R=$CH_2CH_2OH$) (90 mg, 0.5 mmol) was dissolved in water/EtOH (4:1, 2.5 mL) and treated with 9-deazaadenine (62 mg, 0.46 mmol) and aqueous formaldehyde (33 μL, 0.46 mmol) and the mixture left stirring at room temperature for 72 h. The crude reaction was absorbed onto silica and purified on silica gel eluting (eluent 20% [7N $NH_3$ in MeOH] in $CHCl_3$=>5:4.5:0.5 $CHCl_3$:MeOH:$NH_4OH$) to afford a white solid which was dissolved in 2-propanol to afford the title compound 10 (63 mg, 39%) as a crystalline white solid. $^1$H NMR (500 MHz, MeOD): δ=8.16 (s, 1H), 7.49 (s, 1H), 3.96 (dt, J=6.4, 4.3 Hz, 1H), 3.84 (d, J=13.5 Hz, 1H), 3.80 (d, J=13.5 Hz, 1H), 3.66 (t, J=6.8 Hz, 1H), 3.04 (dd, J=9.7, 7.9 Hz, 1H), 2.85 (dd, J=10.3, 6.5 Hz, 1H), 2.76 (dd, J=12.6, 6.4 Hz, 1H), 2.66-2.62 (m, 3H), 2.54 (dd, J=12.7, 8.9 Hz, 1H), 2.38 (dd, J=9.9, 7.1 Hz, 1H), and 2.21-2.14 ppm (m, 1H). $^{13}$C NMR (500 MHz, MeOD): δ=152.1, 151.0, 147.0, 130.1, 115.2, 112.5, 76.8, 62.4, 62.3, 49.3, 49.0, 48.7, 36.0, and 35.6 ppm. ESI-HRMS for $C_{14}H_{22}N_5O_2S$ [MH]$^+$ calcd 324.1494. found 324.1496.

(4S)-1-((4-Amino-5H-pyrrolo[3,2-d]pyrimidin-7-yl) methyl)-4-(((3-hydroxypropyl)thio)methyl)pyrrolidin-3-ol (11)

Amine 5 (R=$CH_2CH_2CH_2OH$) (150 mg, 0.78 mmol) was dissolved in water/EtOH (4:1, 2.5 mL) and treated with 9-deazaadenine (108 mg, 0.78 mmol) and aqueous formaldehyde (62 μL, 0.82 mmol) and the mixture left stirring at room temperature for 72 h. The crude reaction was absorbed onto silica and purified on silica gel eluting (eluent 20%=>30% [7N $NH_3$ in MeOH] in $CHCl_3$) to afford a syrup which crystallised on standing to give the title compound 11 (190 mg, 72%). $^1$H NMR (500 MHz, MeOD): δ=8.18 (s, 1H), 7.49 (s, 1H), 3.98 (dt, J=6.4, 4.1 Hz, 1H), 3.86 (d, J=13.5 Hz, 1H), 3.81 (d, J=13.5 Hz, 1H), 3.62 (t, J=7.3 Hz, 1H), 3.07 (dd, J=9.8, 7.9 Hz, 1H), 2.85 (dd, J=10.3, 6.4 Hz, 1H), 2.74-2.67 (m, 2H), 2.57 (t, J=7.3 Hz, 2H), 2.49 (dd, J=12.7, 9.0 Hz, 1H), 2.38 (dd, J=9.9, 7.2 Hz, 1H), 2.23-2.16 (m, 1H), and 1.76 ppm (quintet, J=6.8 Hz, 2H).$^{13}$C NMR (500 MHz, MeOD): δ=152.1, 151.0, 147.0, 130.1, 115.2, 112.4, 76.8, 62.3, 61.5, 58.9, 49.0, 48.6, 35.8, 33.5, and 29.5 ppm. ESI-HRMS for $C_{15}H_{24}N_5O_2S$ $[MH]^+$ calcd 338.1651. found 338.1648.

(4S)-1-((4-Amino-5H-pyrrolo[3,2-d]pyrimidin-7-yl)methyl)-4-(((4-hydroxybutyl)thio)methyl)pyrrolidin-3-ol (12)

Amine 5 [R=—$(CH_2)_4$OH] (180 mg, 0.88 mmol) was dissolved in water/EtOH (4:1, 2.5 mL) and treated with 9-deazaadenine (121 mg, 0.88 mmol) and aqueous formaldehyde (69 μL, 0.92 mmol) and the mixture left stirring at room temperature for 72 h. The crude reaction was absorbed onto silica and purified on silica gel eluting (eluent 20%=>30% [7N $NH_3$ in MeOH] in $CHCl_3$) to afford a syrup which crystallised on standing to give the title compound 12 (231 mg, 75%). $^1$H NMR (500 MHz, MeOD): δ=8.17 (s, 1H), 7.49 (s, 1H), 3.96 (dt, J=6.4, 4.2 Hz, 1H), 3.85 (d, J=13.5 Hz, 1H), 3.80 (d, J=13.5 Hz, 1H), 3.55 (t, J=6.1 Hz, 1H), 3.32 (quintet, J=1.7 Hz, 1H), 3.05 (dd, J=9.8, 8.0 Hz, 1H), 2.84 (dd, J=10.3, 6.4 Hz, 1H), 2.72 (dd, J=12.7, 6.1 Hz, 1H), 2.67 (dd, J=10.3, 4.2 Hz, 1H), 2.53-2.46 (m, 4H), 2.37 (dd, J=9.9, 7.2 Hz, 1H), 2.22-2.15 (m, 1H), and 1.66-1.56 ppm (m, 4H). $^{13}$C NMR (500 MHz, MeOD): δ=152.1, 151.0, 147.0, 130.1, 115.2, 112.4, 76.8, 62.5, 62.3, 58.9, 49.0, 48.6, 35.8, 33.0, 32.8, and 27.1 ppm. ESI-HRMS for $C_{16}H_{26}N_5O_2S$ $[MH]^+$ calcd 352.1807. found 353.1801.

(4S)-1-((4-Amino-5H-pyrrolo[3,2-d]pyrimidin-7-yl)methyl)-4-(((2-(2-hydroxyethoxy)ethyl)thio)methyl)pyrrolidin-3-ol (13)

Amine 5 (R=$CH_2CH_2OCH_2CH_2OH$) (151 mg, 0.68 mmol) was dissolved in water/EtOH (4:1, 2.5 mL) and treated with 9-deazaadenine (83 mg, 0.62 mmol) and aqueous formaldehyde (45 μL, 0.62 mmol) and the mixture left stirring at room temperature for 72 h. The crude reaction was absorbed onto silica and purified on silica gel eluting (eluent 5:4.8:0.2 $CHCl_3$:MeOH:$NH_4OH$) to afford a white solid which was triturated with 2-propanol to afford the title compound 10 (191 mg, 66%) as a white solid. $^1$H NMR (500 MHz, $D_2O$): δ=7.99 (s, 1H), 7.27 (s, 1H), 3.91 (m, 1H), 3.61 (brs, 4H), 3.52 (brt, J=6.0 Hz, 2H), 3.49-3.46 (m, 2H), 2.89 (t, J=8.9 Hz, 1H), 2.79-2.73 (m, 1H), 2.63-2.54 (m, 4H), 2.38 (t, J=10.5 Hz, 1H, 2.20 (t, J=8.3 Hz, 1H), and 2.10-2.02 ppm (m, 1H). $^{13}$C NMR (500 MHz, $D_2O$): δ=150.1, 149.5, 145.1, 129.6, 113.2, 109.4, 75.1, 71.5, 69.4, 60.4, 59.8, 56.4, 46.8, 46.3, 34.0, and 30.9 ppm. ESI-HRMS for $C_{16}H_{26}N_5O_3S$ $[MH]^+$ calcd 368.1756. found 368.1755.

Synthesis of (3R,4S)-1-({4-amino-5H-pyrrolo[3,2-d]pyrimidin-7-yl}methyl)-4-[(hex-5-yn-1-ylthio)methyl]pyrrolidin-3-ol (14) (Scheme 3).

Scheme 3.

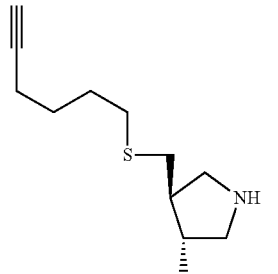

(5) R = hex-5-yn-1-yl

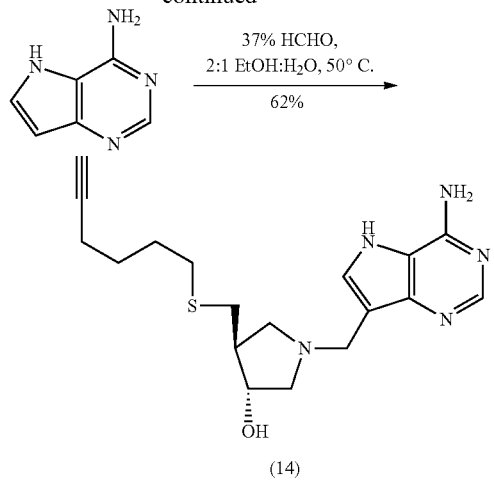

(3R,4S)-4-[(Hex-5-yn-1-ylthio)methyl]pyrrolidin-3-ol (5, R=hex-5-yn-1-yl)

Sodium hydride (120 mg, 2.9 mmol, 60 wt % in oil) was added to a solution of (3R,4S)-tert-butyl 3-hydroxy-4-(methylsulfonyloxymethyl)pyrrolidine-1-carboxylate (3) (500 mg, 1.70 mmol) and hex-5-yne-1-thiol (0.46 mmol, 3.4 mmol) in DMF (5 mL) and the mixture stirred for 1 h. The crude reaction mixture was diluted with diethyl ether and washed with water and brine, dried ($MgSO_4$) and concentrated in vacuo. The crude residue, presumably (3S,4R)-tert-butyl 3-(hex-5-yn-1-ylthiomethyl)-4-hydroxy-pyrrolidine-1-carboxylate, was committed to the next step without purification or characterisation. Conc HCl (2 mL) was added to a solution of (3S,4R)-tert-butyl 3-(hex-5-yn-1ylthiomethyl)-4-hydroxy-pyrrolidine-1-carboxylate (530 mg, 1.7 mmol) in methanol (4 mL) and the mixture concentrated in vacuo. The resulting residue was dissolved in additional conc HCl (2 mL) and concentrated in vacuo. The residue was dissolved in methanol, absorbed onto silica gel, concentrated in vacuo and the solid residue purified by chromatography (1%=>20% [7N NH3 in MeOH] in $CHCl_3$) to afford 5 (R=hex-5-yn-1-yl) (279 mg, 77%) as a yellow syrup. $^1$H NMR (500 MHz, $CDCl_3$): δ=4.08 (dt, J=5.3, 3.3 Hz, 1H), 3.31 (dd, J=10.4, 7.7 Hz, 1H), 3.00 (dd, J=11.9, 5.3 Hz, 1H), 2.87 (dd, J=11.9, 3.1 Hz, 1H), 2.61-2.50 (m, 5H), 2.22 (td, J=6.9, 2.6 Hz, 1H), 1.97 (t, J=2.7 Hz, 1H), 1.75-1.69 (m, 2H) and 1.66-1.60 ppm (m, 2H). $^{13}$C NMR (500 MHz, CDCl3): δ=84.0, 77.2, 68.7, 54.8, 51.6, 48.4, 34.8, 31.9, 28.5, 27.4, and 18.0 ppm. ESI-HRMS for $C_{11}H_{20}NOS$ $[MH]^+$ calcd 214.1265. found 214.1265.

(3R,4S)-1-({4-Amino-5H-pyrrolo[3,2-d]pyrimidin-7-yl}methyl)-4-[(hex-5-yn-1-ylthio)methyl]pyrrolidin-3-ol (14)

Aqueous formaldehyde (176 μL, 234 mmol, 37%) was added to a suspension of 9-deazaadenine (162 mg, 1.17 mmol) and compound 5 (R=hex-5-yn-1-yl) (250 mg, 1.17 mmol) in a mixture of ethanol (4 mL) and water (2 mL) and the resulting suspension warmed to 50° C. After 90 min the reaction was complete as indicated by TLC analysis. The crude reaction was absorbed onto silica gel and concentrated in vacuo. The solid residue was purified by chromatography (20% MeOH in $CHCl_3$=>1% aq $NH_4OH$ in 20% MeOH in CHCl$_3$=>5:4:1 CHCl$_3$:MeOH:NH$_4$OH) to afford the title compound 14 (262 mg, 62%) as a white solid. $^1$H NMR (500 MHz, MeOD): δ=8.18 (s, 1H), 7.48 (s, 1H), 3.97 (dt, J=6.4, 4.2 Hz, 1H), 3.84 (d, J=13.5 Hz, 1H), 3.79 (d, J=13.5 Hz, 1H), 3.05 (dd, J=9.7, 8.0 Hz, 1H), 2.83 (dd, J=10.3, 6.4 Hz, 1H), 2.72 (dd, J=12.8, 6.1 Hz, 1H), 2.67 (dd, J=10.3, 4.1 Hz, 1H), 2.49 (m, 3H), 2.36 (dd, J=9.8, 7.2 Hz, 1H), 2.20 (t, J=2.6 Hz, 1H), 2.18 (m, 1H), 2.16 (td, J=6.9, 2.4 Hz, 2H), 1.16 (m, 2H) and 1.56 ppm (m, 2H). $^{13}$C NMR (500 MHz, MeOD): δ=152.1, 151.0, 147.0, 130.0, 115.2, 112.7, 84.8, 76.9, 69.8, 62.4, 59.0, 49.0, 48.7, 35.8, 32.6, 29.6, 28.7, and 18.7 ppm. ESI-HRMS for C$_{18}$H$_{26}$N$_5$OS [MH]$^+$ calcd 360.1858. found 360.1852.

Synthesis of (3R,4S)-1-({4-amino-5H-pyrrolo[3,2-d]pyrimidin-7-yl}methyl)-4-{2-[(2-hydroxyethyl)thio]ethyl}pyrrolidin-3-ol (16) (Scheme 4).

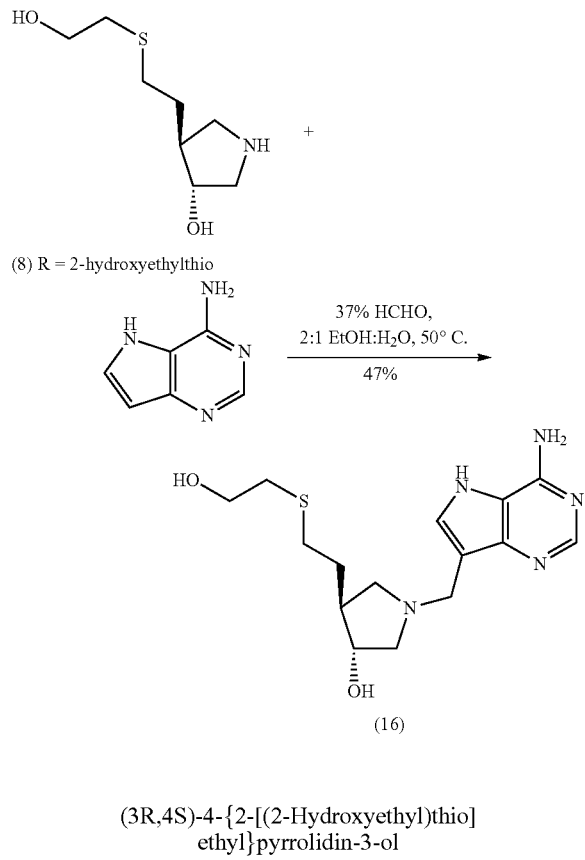

(3R,4S)-4-{2-[(2-Hydroxyethyl)thio]ethyl}pyrrolidin-3-ol (8, R=2-hydroxyethylthio). Sodium hydride (29 mg, 0.73 mmol, 60 wt % in oil) was added to a solution of (3R,4S)-tert-butyl 3-[tert-butyl(dimethyl)silyl]oxy-4-(2-methylsulfonyloxyethyl)pyrrolidine-1-carboxylate (7) (123 mg, 0.29 mmol) and 2-mercaptoethanol (61 μL, 0.87 mmol) in DMF (5 mL) and the mixture stirred for 1 h. The crude reaction mixture was diluted with diethyl ether and washed with water and brine, dried (MgSO$_4$) and concentrated in vacuo. The crude residue was purified by chromatography (25=>40% ethyl acetate in petroleum ether) to afford, presumably (3R,4S)-tert-butyl 3-[(tert-butyldimethylsilyl)oxy]-4-{2-[(2-hydroxyethyl)thio]ethyl}pyrrolidine-1-carboxylate (73 mg), which was committed to the next step without characterisation. Conc HCl (3 mL) was added to a solution of (3R,4S)-tert-butyl 3-[(tert-butyldimethylsilyl)oxy]-4-{2-[(2-hydroxyethyl)thio]ethyl}pyrrolidine-1-carboxylate (73 mg, 0.18 mmol) in methanol (3 mL) and the mixture concentrated in vacuo. The resulting residue was dissolved in additional conc HCl (2 mL) and concentrated in vacuo. The residue was partitioned between water and CHCl$_3$ and the water layer absorbed onto silica, concentrated in vacuo and the resulting solid purified by chromatography (20=>30% [7N NH$_3$ in MeOH] in CHCl$_3$) to afford 8 (R=2-hydroxyethylthio) (29 mg, 84%) as a white solid. $^1$H NMR (500 MHz,CD$_3$OD): δ=4.21 (dt, J=5.0, 3.6 Hz, 1H), 3.69 (t, J=6.6 Hz, 2H), 3.58 (dd, J=11.8, 7.4 Hz, 1H), 3.40 (dd, J=12.3, 5.1 Hz, 1H), 3.15 (dd, J=12.2, 3.1 Hz, 1H), 3.05 (dd, J=11.8, 5.9 Hz, 1H), 2.69-2.64 (m, 4H), 2.41-2.34 (m, 1H), 1.84-1.77 (m, 1H), and 1.65-1.58 ppm (m, 1H). $^{13}$C NMR (500 MHz, CD$_3$OD): δ=75.0, 62.6, 52.5, 49.8, 46.5, 35.2, 32.2, and 30.9 ppm. ESI-HRMS for C$_8$H$_{18}$NO$_2$S [MH]$^+$ calcd 192.1058. found 192.1055.

(3R,4S)-1-({4-Amino-5H-pyrrolo[3,2-d]pyrimidin-7-yl}methyl)-4-{2-[(2-hydroxyethyl)thio]ethyl}pyrrolidin-3-ol (16)

Aqueous formaldehyde (56 μL, 0.75 mmol, 37%) was added to a suspension of 9-deazaadenine (52 mg, 0.38 mmol) and compound 8 (R=2-hydroxyethylthio) (72 mg, 0.38 mmol) in a mixture of ethanol (4 mL) and water (2 mL) and the resulting suspension warmed to 60° C. After 2 h the reaction was complete as indicated by TLC analysis. The crude reaction was absorbed onto silica gel and concentrated in vacuo. The solid residue was purified by chromatography (30% MeOH in CHCl$_3$) to afford the title compound 16 (58 mg, 47%) as a white solid. $^1$H NMR (500 MHz,D$_2$O): δ=8.09 (s, 1H), 7.49 (s, 1H), 3.98 (q, J=4.4 Hz, 1H), 3.92 (s, 2H), 3.65 (t, J=6.3 Hz, 2H), 3.18 (dd, J=10.6, 8.1 Hz, 1H), 2.99 (dd, J=11.3, 6.3 Hz, 1H), 2.81 (dd, J=11.3, 3.9 Hz, 2H), 2.61 (t, J=6.2 Hz, 2H), 2.46 (t, J=7.6 Hz, 1H), 2.46 (m, 1H), 2.06 (m, 1H), 1.70-1.63 (m, 1H), and 1.47-1.41 ppm (m, 1H). $^{13}$C NMR (500 MHz, D$_2$O): δ=150.5, 150.0, 145.2, 130.4, 113.5, 107.8, 75.0, 60.3, 59.1, 56.3, 47.1, 45.3, 33.3, 31.7, and 29.3 ppm. ESI-HRMS for C$_{15}$H$_{24}$N$_5$O$_2$S [MH]$^+$ calcd 338.1651. found 338.1645.

Synthesis of (3R,4S)-1-({4-amino-5H-pyrrolo[3,2-d]pyrimidin-7-yl}methyl)-4-(2-{[2-(2-hydroxyethoxyl)ethyl]thio}ethyl)pyrrolidin-3-ol (17) (Scheme 5).

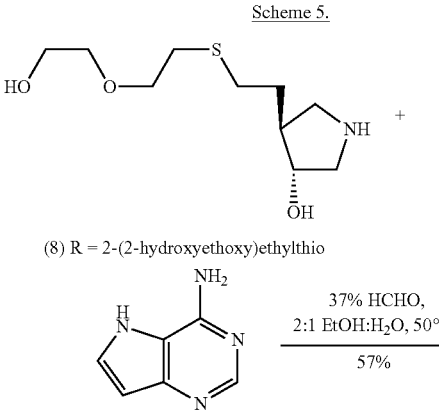

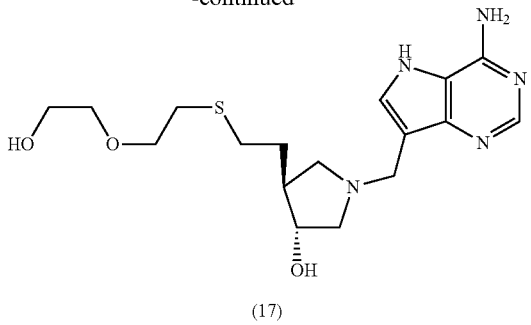

(17)

(3R,4S)-4-(2-{[2-(2-Hydroxyethoxyl)ethyl]thio}ethyl)pyrrolidin-3-ol[8, R=2-(2-hydroxyethoxyl)ethylthio]

Sodium hydride (94 mg, 2.36 mmol, 60 wt % in oil) was added to a solution of (3R,4S)-tert-butyl 3-[tert-butyl(dimethyl)silyl]oxy-4-(2-methylsulfonyloxyethyl)pyrrolidine-1-carboxylate (7) (400 mg, 0.94 mmol) and 2-mercaptoethoxy ethanol (319 µL, 2.83 mmol) in DMF (10 mL) and the mixture stirred for 14 h. The crude reaction mixture was diluted with diethyl ether and washed with water and brine, dried (MgSO$_4$) and concentrated in vacuo. The crude residue was purified by chromatography (40% ethyl acetate in petroleum ether) to afford, presumably (3R,4S)-tert-butyl 3-[(tert-butyldimethylsilyl)oxy]-4-(2-{[2-(2-hydroxyethoxy)ethyl)]thio}ethyl)pyrrolidine-1-carboxylate (402 mg, 94%), which was committed to the next step without characterisation. Tetrabutylammonium fluoride (TBAF) in THF (1 mL, 1 mol/L) was added to a solution of (3R,4S)-tert-butyl 3-[(tert-butyldimethylsilyl)oxy]-4-(2-{[2-(2-hydroxyethoxyl)ethyl]thio}ethyl)pyrrolidine-1-carboxylate (200 mg, 0.44 mmol) in THF (4 mL) and the resulting solution stirred for 14 h. The mixture was concentrated in vacuo and the residue purified by chromatography (ethyl acetate=>5% MeOH in CHCl$_3$) to afford (3R,4S)-tert-butyl 3-hydroxy-4-{2-[2-(2-hydroxyethoxyl)ethylthio]ethyl}pyrrolidine-1-carboxylate (94 mg, 63%) as a colourless syrup which was committed to the next step without characterisation. Trifluoroacetic acid (TFA) (1 mL, 13.0 mmol, 99.9 mass %, 1 mL, 1.489 g) was added to a solution of (3R,4S)-tert-butyl 3-hydroxy-4-{2-[2-(2-hydroxyethoxyl)ethylthio]ethyl}pyrrolidine-1-carboxylate (94 mg, 0.28 mmol) in CHCl$_3$ (10 mL) and the mixture left stirring for 2 h. The mixture was concentrated in vacuo and the residue purified by chromatography (30% [7N NH$_3$ in MeOH] in CHCl$_3$) to afford 8 [R=2-(2-hydroxyethoxyl)ethylthio] (70 mg, 106%) as a syrup. $^1$H NMR (500 MHz, CD$_3$OD): δ=4.21 (dt, J=5.1, 3.5 Hz, 1H), 3.68-3.65 (m, 4H), 3.58 (dd, J=11.8, 7.4 Hz, 1H), 3.56-3.54 (m, 2H), 3.40 (dd, J=8.6, 5.2 Hz, 1H), 3.15 (dd, J=12.3, 3.2 Hz, 1H), 3.04 (dd, J=11.8, 6.0 Hz, 1H), 2.73 (t, J=6.6 Hz, 2H), 2.69-2.65 (m, 2H), 2.40-2.34 (m, 1H), 1.83-1.76 (m, 1H), and 1.64-1.57 ppm (m, 1H). $^{13}$C NMR (500 MHz, CD$_3$OD): δ=75.1, 73.4, 72.2, 62.3, 52.4, 49.7, 46.5, 32.3, 32.1, and 31.1 ppm. ESI-HRMS for C$_{10}$H$_{22}$NO$_3$S [MH]$^+$ calcd 236.1320. found 236.1319.

(3R,4S)-1-({4-Amino-5H-pyrrolo[3,2-d]pyrimidin-7-yl}methyl)-4-(2-{[2-(2-hydroxyethoxy)ethyl]thio}ethyl)pyrrolidin-3-ol (17)

Aqueous formaldehyde (45 µL, 0.59 mmol, 37%) was added to a solution of 9-deazaadenine (41 mg, 0.30 mmol) and compound 8 [R=2-(2-hydroxyethoxyl)ethylthio] (70 mg, 0.30 mmol) in a mixture of ethanol (4 mL) and water (2 mL) and the resulting suspension warmed to 60° C. After 2 h the reaction was complete as indicated by TLC analysis. The crude reaction was absorbed onto silica gel and concentrated in vacuo. The solid residue was purified by chromatography (eluent 30% MeOH in CHCl$_3$) to afford the title compound 17 (65 mg, 57%) as a white solid. $^1$H NMR (500 MHz, MeOD): δ=8.30 (s, 1H), 7.81 (s, 1H), 4.53 (s, 2H), 4.19-4.16 (m, 1H), 3.77 (dd, J=11.8, 7.8 Hz, 1H), 3.67-3.62 (m, 4H), 3.54-3.50 (m, 3H), 3.33-3.31 (m, 1H), 3.12 (dd, J=11.9, 7.8 Hz, 1H), 2.68 (t, J=6.6 Hz, 2H), 2.60 (t, J=7.3 Hz, 2H), 2.40-2.36 (m, 1H), 1.85-1.78 (m, 1H), and 1.61-1.54 ppm (m, 1H). $^{13}$C NMR (500 MHz, CD$_3$OD): δ=152.6, 150.8, 145.1, 133.1, 115.3, 105.1, 74.8, 73.4, 72.2, 62.3, 60.2, 57.6, 49.4, 46.6, 32.5, 32.3, and 31.1 ppm. ESI-HRMS for C$_{17}$H$_{28}$N$_5$O$_3$S [MH]$^+$ calcd 382.1913. found 382.1906.

Synthesis of (3R,4S)-1-({4-amino-5H-pyrrolo[3,2-d]pyrimidin-7-yl}methyl)-4-[(hexylthio)methyl]pyrrolidin-3-ol (18) (Scheme 6).

Scheme 6.

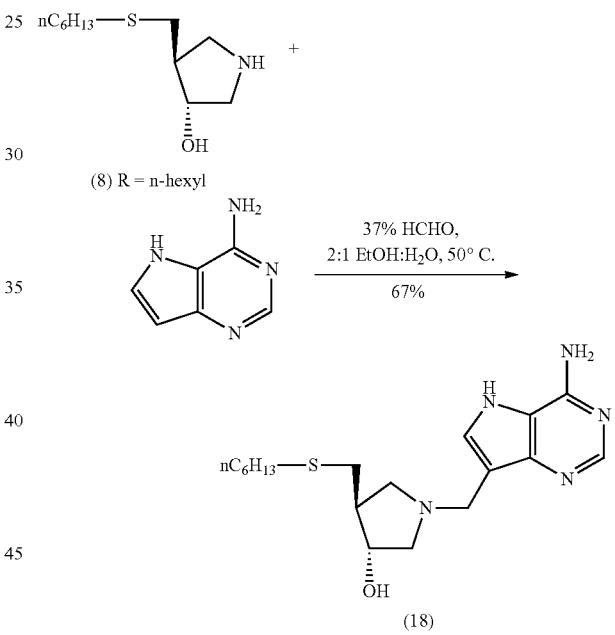

(18)

(3R,4S)-4-[(Hexylthio)methyl]pyrrolidin-3-ol (5, R=n-Hexyl)

Sodium hydride (115 mg, 2.88 mmol, 60 mass %) was added to a solution of (3R,4S)-tert-butyl 3-hydroxy-4-(methylsulfonyloxymethyl)pyrrolidine-1-carboxylate (425 mg, 1.44 mmol) and 1-hexanethiol (0.624 µL 4.32 mmol) in DMF (10 mL) and the mixture stirred for 14 h. The crude reaction mixture was diluted with diethyl ether and washed with water and brine, dried (MgSO$_4$) and concentrated in vacuo. The crude residue, presumably (3S,4R)-tert-butyl 3-(n-hexylthiomethyl)-4-hydroxy-pyrrolidine-1-carboxylate, was committed to the next step without purification or characterisation. Conc HCl (3 mL) was added to a solution of (3S,4R)-tert-butyl 3-(n-hexylthiomethyl)-4-hydroxy-pyrrolidine-1-carboxylate (457 mg, 1.44 mmol) in methanol (3 mL) and the mixture concentrated in vacuo. The resulting residue was dissolved in additional conc HCl (3 mL) and concentrated in vacuo. The residue was dissolved in methanol and absorbed onto silica, concentrated in vacuo and the resulting solid purified by chromatography (10=>20% 7N NH$_3$ in CHCl$_3$) to afford 5 (R=n-hexyl) (221 mg, 72%) as a white solid. $^1$H NMR (500 MHz, CD$_3$OD): δ=4.03 (dt, J=5.5, 3.6 Hz, 1H), 3.21 (dd, J=11.5, 7.5 Hz, 1H), 2.98 (dd, J=12.1, 5.6 Hz, 1H), 2.74 (dd, J=12.0, 3.5 Hz, 1H), 2.66 (dd, J=12.8, 6.6 Hz, 1H), 2.61 (dd, J=11.6, 5.9 Hz, 1H), 2.54 (brt, J=7.3 Hz, 2H), 2.44 (dd, J=12.7, 8.7 Hz, 1H), 2.17-2.10 (m, 1H), 1.60-1.55 (m, 2H), 1.43-1.38 (m, 2H), 1.34-1.28 (m, 4H), and 0.91 ppm (t, J=7.0 Hz, 3H). $^{13}$C NMR (500 MHz, CD$_3$OD): δ=77.9, 54.9, 51.6, 49.3, 35.3, 33.2, 32.6, 30.8, 29.6, 23.7, and 14.4 ppm. ESI-HRMS for C$_{11}$H$_{24}$NOS [MH]$^+$ calcd 218.1579. found 218.1578.

(3R,4S)-1-({4-Amino-5H-pyrrolo[3,2-d]pyrimidin-7-yl}methyl)-4-[(hexylthio)methyl]pyrrolidin-3-ol (18)

Aqueous formaldehyde (120 µL, 1.70 mmol, 37%) was added to a solution of 9-deazaadenine (110 mg, 0.83 mmol) and compound 5 (R=n-hexyl) (180 mg, 0.83 mmol) in a mixture of ethanol (4 mL) and water (2 mL) and the resulting suspension warmed to 60° C. After 2 h the reaction was complete as indicated by TLC analysis. The crude reaction was absorbed onto silica gel and concentrated in vacuo. The solid residue was purified by chromatography (5=>10=>20% MeOH in CHCl$_3$) to afford the title compound the title compound 18 (201 mg, 67%) as a white solid. $^1$H NMR (500 MHz, CD$_3$OD): δ=8.16 (s, 1H), 7.49 (s, 1H), 3.95 (dt, J=4.4, 4.2 Hz, 1H), 3.84 (d, J=13.4 Hz, 1H), 3.79 (d, J=13.4 Hz, 1H), 3.04 (dd, J=9.7, 8.1 Hz, 1H), 2.84 (dd, J=10.3, 6.5 Hz, 1H), 2.72 (dd, J=12.7, 6.0 Hz, 1H), 2.65 (dd, J=10.2, 4.2 Hz, 1H), 2.50-2.47 (m, 3H), 2.37 (dd, J=9.8, 7.2 Hz, 1H), 2.20-2.15 (m, 1H), 1.54 (br quintet, J=7.2 Hz, 1H), 2.16 (td, J=6.9, 2.4 Hz, 2H), 1.16 (m, 2H) and 1.56 ppm (m, 2H). $^{13}$C NMR (500 MHz, CD$_3$OD): δ=152.1, 151.0, 147.0, 130.0, 115.2, 112.6, 76.9, 62.3, 58.9, 49.0, 49.0, 35.9, 33.1, 32.6, 30.7, 29.6, 23.6, and 14.4 ppm. ESI-HRMS for C$_{18}$H$_{30}$N$_5$OS [MH]$^+$ calcd 364.2171. found 364.2165.

Synthesis of (3R,4S)-1-({4-amino-5H-pyrrolo[3,2-d]pyrimidin-7-yl}methyl)-4-[2-(hexylthio)ethyl]pyrrolidin-3-ol (19) (Scheme 7).

Scheme 7.

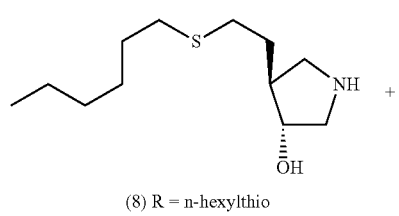

(8) R = n-hexylthio

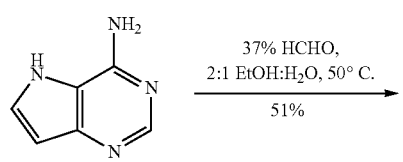

37% HCHO,
2:1 EtOH:H$_2$O, 50° C.
⟶
51%

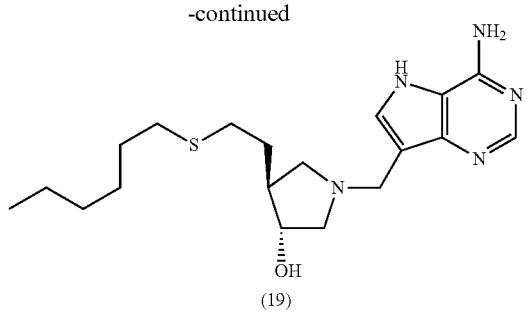

(19)

(3R,4S)-4-(2-(Hexylthio)ethyl)pyrrolidin-3-ol (8, R=n-hexylthio)

Sodium hydride (94 mg, 2.36 mmol, 60 wt % in oil) was added to a solution of (3R,4S)-tert-butyl 3-[tert-butyl(dimethyl)silyl]oxy-4-(2-methylsulfonyloxyethyl)pyrrolidine-1-carboxylate (400 mg, 0.94 mmol) (7) and 1-hexanethiol (530 µL, 0.87 mmol) in DMF (10 mL) and the mixture stirred for 14 h. The crude reaction mixture was diluted with toluene and washed with water and brine, dried (MgSO$_4$) and concentrated in vacuo. The crude residue was purified by chromatography (10% ethyl acetate in petroleum ether) to afford, presumably (3R,4S)-tert-butyl 3-[tert-butyl(dimethyl)silyl]oxy-4-(2-hexylthioethyl)pyrrolidine-1-carboxylate (421 mg, 73%), which was committed to the next step without characterisation. Conc HCl (3 mL) was added to a solution of (3R,4S)-tert-butyl 3-[tert-butyl(dimethyl)silyl]oxy-4-(2-hexylthioethyl)pyrrolidine-1-carboxylate (421 mg, 0.70 mmol) in methanol (3 mL) and the mixture concentrated in vacuo. The resulting residue was dissolved in additional conc HCl (2 mL) and concentrated in vacuo, the residue was partitioned between water and CHCl$_3$ and the water layer absorbed onto silica, concentrated in vacuo and the resulting solid purified by chromatography (20=>30% [7N NH$_3$ in MeOH] in CHCl$_3$) to afford 8 (R=n-hexylthio) (160 mg, 73%) as a white solid. $^1$H NMR (500 MHz, CD$_3$OD+CDCl$_3$): δ=3.97 (dt, J=5.0, 3.0 Hz, 1H), 3.30 (dd, J=11.0, 7.7 Hz, 1H), 3.14 (brs, 2H), 2.96 (dd, J=11.9, 5.1 Hz, 1H), 2.89 (dd, J=11.8, 7.4 Hz, 1H), 2.60-2.54 (m, 2H), 2.51 (t, J=7.5 Hz, 2H), 2.46 (dd, J=11.1, 6.9 Hz, 1H), 2.03 (dquintet, J=7.4, 3.2 Hz, 1H), 1.76-1.69 (m, 1H), 1.60-1.54 (m, 2H), 1.42-1.35 (m, 2H), 1.34-1.28 (m, 2H), and 0.89 ppm (t, J=7.2 Hz, 3H). $^{13}$C NMR (500 MHz, CD$_3$OD+CDCl$_3$): δ=77.6, 54.9, 51.8, 48.2, 32.6, 32.2, 31.4, 30.7, 29.6, 28.6, 22.5, and 14.0 ppm. ESI-HRMS for C$_{12}$H$_{26}$NOS [MH]$^+$ calcd 232.1735. found 232.1736.

(3R,4S)-1-({4-Amino-5H-pyrrolo[3,2-d]pyrimidin-7-yl}methyl)-4-[2-(hexylthio)ethyl]pyrrolidin-3-ol (19)

Aqueous formaldehyde (104 µL, 1.38 mmol, 37%) was added to a solution of 9-deazaadenine (96 mg, 0.69 mmol) and compound 8 (R=n-hexylthio) (160 mg, 0.69 mmol) in a mixture of ethanol (4 mL) and water (2 mL) and the resulting suspension warmed to 60° C. After 2 h the reaction was complete as indicated by TLC analysis. The crude reaction was absorbed onto silica gel and concentrated in vacuo. The solid residue was purified by chromatography (20% MeOH in CHCl$_3$) to afford the title compound 19 (132 mg, 51%) as a white solid. $^1$H NMR (500 MHz, CD$_3$OD+CDCl$_3$): δ=8.20 (s, 1H), 7.44 (s, 1H), 3.89 (q, J=4.9 Hz, 1H), 3.85 (d, J=13.5 Hz, 1H), 3.81 (d, J=13.5 Hz, 1H), 3.11 (dd, J=9.4, 7.7 Hz, 1H), 2.75 (brd, J=12.4 Hz, 2H), 2.52 (t, J=7.4 Hz, 2H), 2.50 (t, J=7.4 Hz, 2H), 2.18 (dd, J=9.3, 8.1 Hz, 1H), 2.14-2.07 (m, 1H), 1.85-1.78 (m, 1H), 1.64-1.53 (m, 3H), 1.41-1.34 (m, 2H), 1.33-1.24 (m, 4H), 0.89 (t, J=6.9 Hz, 3H) and 1.56 ppm (m, 2H). $^{13}$C NMR (500 MHz, CD$_3$OD+CDCl$_3$): δ=151.9, 151.0, 147.1, 129.8, 115.3, 112.7, 77.6, 62.5, 59.6, 49.4, 48.2, 34.5, 33.2, 32.7, 31.6, 30.8, 29.7, 23.7, and 14.8 ppm. ESI-HRMS for C$_{19}$H$_{32}$N$_5$OS [MH]$^+$ calcd 378.2328. found 378.2332.

Synthesis of (3R,4S)-1-({4-amino-5H-pyrrolo[3,2-d]pyrimidin-7-yl}methyl)-4-[(pyridin-2-ylthio)methyl]pyrrolidin-3-ol (24) (Scheme 8).

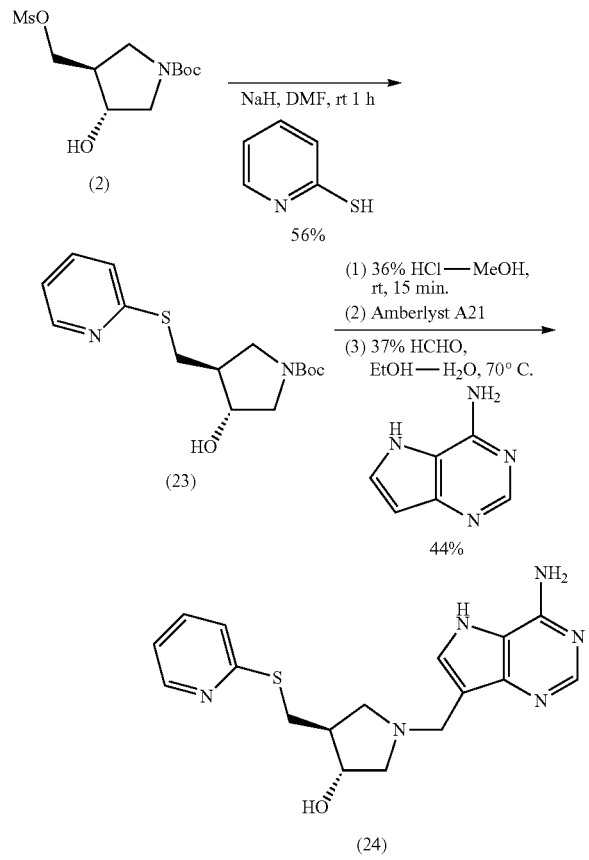

tert-Butyl (3R,4S)-3-hydroxy-4-[(pyridin-2-ylthio)methyl]pyrrolidine-1-carboxylate (23)

Step 1. tert-Butyl (3R,4R)-3-hydroxy-4-(hydroxymethyl)pyrrolidine-1-carboxylate (1) [Clinch, et al.[37]] (10.00 g, 46.03 mmol) and N,N'-diisopropylethylamine (16.2 mL, 92.06 mmol) were dissolved in CH$_2$Cl$_2$ (300 mL) and cooled to −60° C. Methanesulfonyl chloride (3.45 mL, 44.61 mmol) was added dropwise. After 30 min more methanesulfonyl chloride (0.60 mL) added and the mixture stirred a further 5 min then warmed to 0° C. and washed with sat. aq NaHCO$_3$ (3×30 mL), dried and the solvent evaporated. The residue was chromatographed on silica gel (gradient of 50-100% EtOAc in hexanes then 0-1% MeOH in EtOAc) to give the mesylate 2 as a yellow oil (8.18 g, 60%).

Step 2. Sodium hydride (60 wt % in oil, 0.060 g, 1.50 mmol) was added in portions to a stirred solution of pyridine-2-thiol (0.135 g, 1.21 mmol) in DMF (5 mL) at 0° C. After 20 min a solution of the mesylate 2 from step 1 above (0.300 g, 1.02 mmol) in DMF (1 mL) was added and the mixture warmed to room temperature and stirred for 16 h. Water (5 mL) was added then the mixture was extracted with Et$_2$O (60 mL) and the extract washed with H$_2$O (3×5 mL), brine (5 mL), dried and evaporated to a yellow gum/solid. Chromatography on silica gel (gradient of 40-80% EtOAc in hexanes) gave 23 as a colourless gum which solidified on standing for a couple of days (0.175 g, 56%). $^1$H NMR (500 MHz, CDCl$_3$): δ 8.40 (d, J=4.6 Hz, 1H), 7.50 (dt, J=8.1, 1.5 Hz, 1H), 7.25 (dt, J=8.1, 0.9 Hz, 1H), 7.03 (dt, J=5.5, 1.2 Hz, 1H), 4.23 (bs, exchanged D$_2$O, 0.5H), 4.14-4.05 (m, 1.5H, after D$_2$O exchange, m, 1H), 3.76-3.49 (m, 3H), 3.24-3.11 (m, 3H), 2.51-2.39 (m, 1H), 1.45 (s, 9H). $^{13}$C NMR (125.7 MHz, CDCl$_3$, centre line δ 77.0): δ 159.1, 158.9 (C), 154.6, 154.4 (C), 149.3 (CH), 136.3 (CH), 122.9, 122.8 (CH), 119.9 (CH), 79.4 (C), 72.1, 71.7 (CH), 51.1, 50.8 (CH), 48.4, 47.8 (CH$_2$), 46.1, 45.5 (CH$_2$), 29.2, 29.1 (CH$_2$), 28.5 (CH$_3$). ESI-HRMS calcd for C$_{15}$H$_{23}$N$_2$O$_3$S$^+$, (M+H)$^+$, 311.1424. found 311.1424.

(3R,4S)-1-({4-Amino-5H-pyrrolo[3,2-d]pyrimidin-7-yl}methyl)-4-[(pyridin-2-ylthio)methyl]pyrrolidin-3-ol (24)

Compound 23 (0.171 g, 0.55 mmol) was dissolved in MeOH (4 mL) and aq. hydrochloric acid (36%, 1.5 mL) added. After 15 min the solvent was evaporated to yield a colourless gum that was dissolved in MeOH (10 mL), neutralized with Amberlyst A21 resin then passed through a short column of the same resin eluted with MeOH. The solvent was evaporated and the residue dissolved in a mixture of EtOH (4 mL) and H$_2$O (2 mL) to which were added aq. formaldehyde solution (37%, 0.08 mL, 1 mmol) and 9-deazaadenine (0.096 g, 0.72 mmol). The mixture was heated at 70° C. for 16 h and silica gel was added to absorb all the solvent then the solvent was evaporated and the residue purified by chromatography on silica gel (gradient of 0-7% aq. NH$_4$OH (28%) in 2-PrOH). The fractions containing product were evaporated and the residue further chromatographed on silica gel (CHCl$_3$-7M NH$_3$/MeOH, 85:15) to afford 24 as a colourless solid (0.087 g, 44%). $^1$H NMR (500 MHz, 1:1 CD$_3$OD-CDCl$_3$): δ 8.34 (ddd, J=5.0, 1.8, 0.9 Hz, 1H), 8.19 (s, 1H), 7.54 (ddd, J=9.7, 7.7, 1.9 Hz, 1H), 7.41 (s, 1H), 7.23 (dt, J=8.2, 0.9 Hz, 1H), 7.03 (ddd, J=7.3, 5.0, 0.9 Hz, 1H), 4.07 (ddd, J=6.4, 3.9, 3.9 Hz, 1H), 3.85 (d, J=13.5 Hz, 1H), 3.81 (d, J=13.4 Hz, 1H), 3.37-3.34 (m, 1H+residual deuterated solvent), 3.15 (dd, J=13.1, 8.2 Hz, 1H), 3.10-3.06 (m, 1H), 2.87 (dd, J=10.4, 6.4 Hz, 1H), 2.74 (dd, J=10.4, 3.9 Hz, 1H), 2.41-2.33 (m, 2H). $^{13}$C NMR (125.7 MHz, 1:1 CD$_3$OD-CDCl$_3$, centre lines δ 49.0 and δ 78.3): δ 159.8 (C), 151.2 (C), 150.4 (CH), 149.7 (CH), 146.5 (C), 137.2 (CH), 129.1 (CH), 123.0 (CH), 120.4 (CH), 114.7 (C), 112.2 (C), 76.3 (CH), 61.9 (CH$_2$), 58.4 (CH$_2$), 48.7 (CH$_2$), 47.9 (CH), 33.5 (CH$_2$). ESI-HRMS calcd for C$_{17}$H$_{21}$N$_6$OS$^+$, (M+H)$^+$, 357.1493. found 357.1485.

Synthesis of (3R,4S)-1-({4-amino-5H-pyrrolo[3,2-d]pyrimidin-7-yl}methyl)-4-[(pyrazin-2-ylthio)methyl]pyrrolidin-3-ol (27) (Scheme 9).

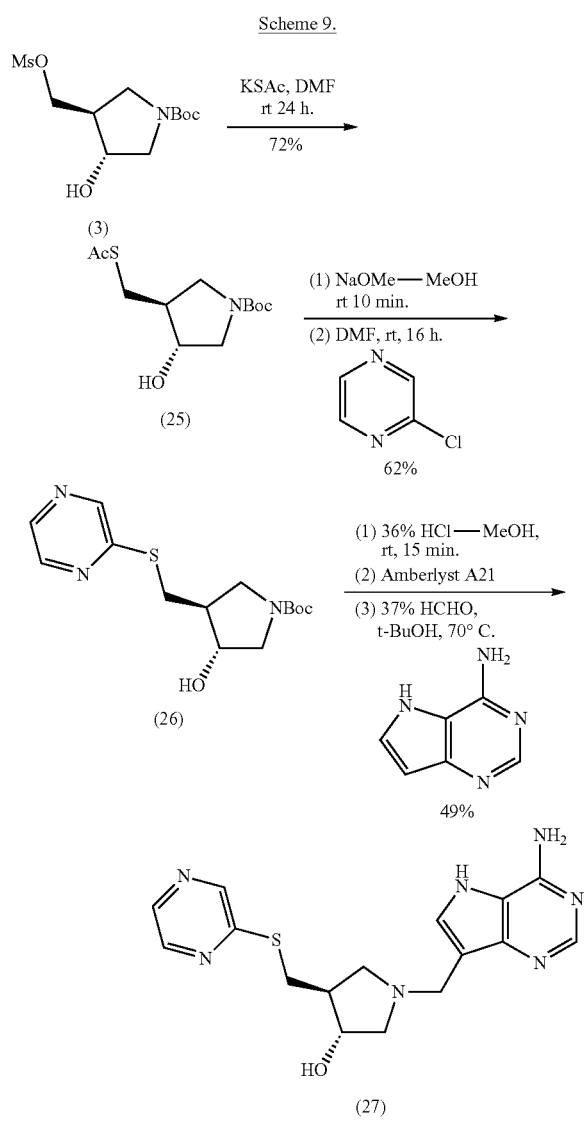

tert-Butyl (3S,4R)-3-[(acetylthio)methyl]-4-hydroxypyrrolidine-1-carboxylate (25)

Potassium thioacetate (0.950 g, 8.15 mmol) and the mesylate 3 (2.00 g, 6.77 mmol) were stirred together in DMF (20 mL) at room temperature for 24 h. Water (15 mL) was added and the mixture extracted with Et$_2$O (120 mL). The extract was washed with H$_2$O (3×15 mL) then brine (15 mL), dried and the solvent evaporated to a colourless residue that was chromatographed on silica gel (gradient of 40-70% EtOAc in hexanes) to give 25 as a colourless oil (1.54 g, 83%). $^1$H NMR (500 MHz, CDCl$_3$): δ 4.02 (bs, 1H), 3.71-3.54 (m, 2H), 3.28-3.17 (m, 1H), 3.15-3.04 (m, 1H), 3.02-2.90 (m, 2H), 2.74 (s, exchanged D$_2$O, 1H), 2.37 (s, 3H), 2.35-2.25 (m, 1H), 1.45 (s, 9H). $^{13}$C NMR (125.7 MHz, CDCl$_3$, centre line δ 77.0): δ 196.5, 191.1 (C), 154.5 (C), 79.6 (C), 73.3, 72.8 (CH), 52.0, 51.7 (CH$_2$), 48.6, 48.0 (CH$_2$), 46.0, 45.4 (CH), 30.6 (CH$_3$), 29.2, 29.1 (CH$_2$), 25.5 (CH$_3$). ESI-HRMS calcd for C$_{12}$H$_{21}$NO$_4$S$^+$, (M+Na)$^+$, 298.1084. found 298.1087.

tert-Butyl (3R,4S)-3-hydroxy-4-[(pyrazin-2-ylthio)methyl]pyrrolidine-1-carboxylate (26)

Sodium methoxide in methanol solution (25%, 0.21 mL, 0.92 mmol) was added to a stirred solution of 25 (0.250 g, 0.91 mmol) in MeOH (5 mL). After 10 min the solvent was evaporated and the residue dissolved in DMF (4 mL), then 2-chloropyrazine (0.24 mL, 2.7 mmol) added and the mixture stirred at room temperature for 16 h. Water (5 mL) was added and the mixture extracted with Et$_2$O (60 mL). The extract was washed with H$_2$O (3×15 mL), brine (15 mL), dried and the solvent evaporated. The residue was chromatographed on silica gel (gradient of 40-80% EtOAc in hexanes) to give 26 as a colourless gum (0.175 g, 62%). $^1$H NMR (500 MHz, CDCl$_3$): δ 8.50 (d, J=1.5 Hz, 1H), 8.34 (s, 1H), 8.25 (d, J=2.7 Hz, 1H), 4.17-4.12 (m, 1H), 3.75-3.59 (m, 2H), 3.41-3.13 (m, 5H, after D$_2$O exchange, 4H), 2.52-2.41 (m, 1H), 1.45 (s, 9H). $^{13}$C NMR (125.7 MHz, CDCl$_3$, centre line δ 77.0): δ 156.6, 156.5 (C), 154.5 (C), 144.2 (CH), 143.7 (CH), 139.8 (CH), 79.6 (C), 73.2, 72.7 (CH), 51.8, 51.6 (CH$_2$), 48.7, 48.1 (CH$_2$), 46.0, 45.4 (CH), 29.7, 29.5 (CH$_2$), 28.5 (CH$_3$). ESI-HRMS calcd for C$_{14}$H$_{21}$N$_3$NaO$_3$S$^+$, (M+Na)$^+$, 334.1196. found 334.1193.

(3R,4S)-1-({4-Amino-5H-pyrrolo[3,2-d]pyrimidin-7-yl}methyl)-4-[(pyrazin-2-ylthio)methyl]pyrrolidin-3-ol (27)

Compound 26 (0.155 g, 0.50 mmol) was dissolved in MeOH (4 mL, 97.8 mmol) and aq. hydrochloric acid (36%, 1.5 mL) added. After 15 min the solvent was evaporated and the residue was dissolved in MeOH (10 mL) and neutralized with Amberlyst A21 resin then passed through a short column of the same resin eluted with MeOH. The residue was dissolved in a mixture of ethanol (4 mL) and H$_2$O (2 mL), then aq. formaldehyde solution (37%, 0.075 mL, 1.0 mmol) and 9-deazaadenine (0.080 g, 0.60 mmol) added and the mixture heated at 70° C. for 16 h. Silica gel was added to absorb all the solvent then the solvent was evaporated and the residue purified by chromatography on silica gel (0-10% aq. NH$_4$OH (28%) in 2-PrOH) to give 27 as a colourless solid (70 mg, 30%) together with a less pure fraction (34 mg, 19%). $^1$H NMR (500 MHz, CD$_3$OD): δ 8.43 (d, J=1.5 Hz, 1H), 8.37 (dd, J=2.6, 1.6 Hz, 1H), 8.19 (d, J=2.7 Hz, 1H), 8.13 (s, 1H), 7.47 (s, 1H), 4.04 (ddd, J=6.4, 4.2, 4.2 Hz, 1H), 3.85 (d, J=13.6 Hz, 1H), 3.80 (d, J=13.4 Hz, 1H), 3.41 (dd, J=13.3, 6.4 Hz, 1H), 3.22 (dd, J=13.3, 8.3 Hz, 1H), 3.02 (dd, J=9.6, 7.8 Hz, 1H), 2.90 (dd, J=10.3, 6.5 Hz, 1H), 2.66 (dd, J=10.3, 4.2 Hz, 1H), 2.42 (dd, J=9.7, 7.0 Hz, 1H), 2.34 (m, 1H). $^{13}$C NMR (125.7 MHz, CD$_3$OD, centre line δ 49.0): δ 158.5 (C), 152.1 (C), 151.0 (CH), 147.0 (CH), 145.4 (CH), 144.6 (CH), 140.4 (CH), 130.1 (CH), 115.1 (C), 112.4 (C), 76.7 (CH), 62.3 (CH$_2$), 58.5 (CH$_2$), 48.8 (CH$_2$), 48.3 (CH), 32.9 (CH$_2$). ESI-HRMS calcd for C$_{16}$H$_{20}$N$_7$OS$^+$, (M+H)$^+$, 358.1445. found 358.1442.

Synthesis of (3R,4S)-1-({4-amino-5H-pyrrolo[3,2-d]pyrimidin-7-yl}methyl)-4-[(1,3-thiazol-2-ylthio)methyl]pyrrolidin-3-ol (29) (Scheme 10).

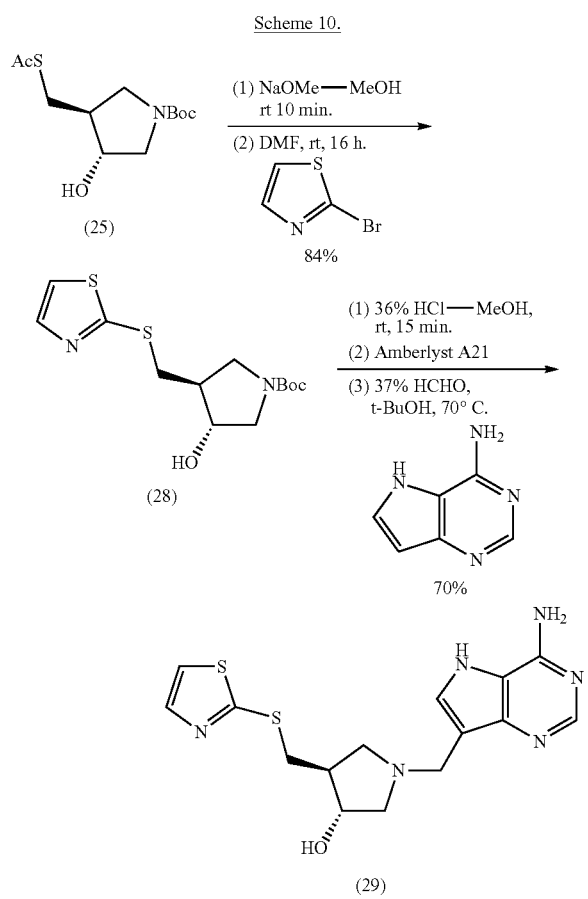

tert-Butyl (3R,4S)-3-hydroxy-4-[(1,3-thiazol-2-ylthio)methyl]pyrrolidine-1-carboxylate (28)

Sodium methoxide in methanol solution (25%, 0.21 mL, 0.92 mmol) was added to a solution of 25 (0.250 g, 0.91 mmol) in MeOH (5 mL). After 10 min the solvent was evaporated and residue dissolved in DMF (4 mL) then 2-bromothiazole (0.25 mL, 2.8 mmol) added and the mixture stirred at room temperature for 60 h. Water (5 mL) was added then the mixture extracted with Et$_2$O (60 mL). The extract was washed with H$_2$O (3×5 mL), brine (5 mL), dried and evaporated. The residue was chromatographed on silica gel (gradient of 40-80% EtOAc-hexanes) to give 28 as a colourless oil (0.230 g, 80%). $^1$H NMR (500 MHz, CDCl$_3$): δ 7.642, 7.636 (2s, 1H), 7.241, 7.235 (2s, 1H), 4.34 (bs, exchanged D$_2$O, 0.5H), 4.21-4.12 (m, 1.5H, after D$_2$O exchange, m, 1H), 3.76-3.56 (m, 2H), 3.55-3.42 (m, 1H), 3.29-3.12 (m, 3H), 2.49 (m, 1H), 1.45 (s, 9H). $^{13}$C NMR (125.7 MHz, CDCl$_3$, centre line δ 77.0): δ 165.8, 165.4 (C), 154.6, 154.4 (C), 142.3, 142.2 (CH), 119.4 (CH), 79.5 (C), 72.3, 71.9 (CH), 51.3, 51.0 (CH$_2$), 48.4, 47.8 (CH$_2$), 46.0, 45.4 (CH), 34.0, 33.8 (CH$_2$), 28.4 (CH$_3$). ESI-HRMS calcd for C$_{13}$H$_{20}$N$_2$NaO$_3$S$_2^+$, (M+Na)$^+$, 339.0808. found 339.0802.

(3R,4S)-1-({4-Amino-5H-pyrrolo[3,2-d]pyrimidin-7-yl}methyl)-4-[(1,3-thiazol-2-yl]thio)methyl]pyrrolidin-3-ol (29)

Compound 28 (0.210 g, 0.66 mmol) was dissolved in MeOH (4 mL) and aq. hydrochloric acid (36%, 1.5 mL) added. After 15 min the solvent was evaporated to give a solid that was dissolved in MeOH (10 mL), neutralized with Amberlyst A21 resin then passed through a short column of the same resin eluting with MeOH. The solvent was evaporated and the residue dissolved in a mixture of ethanol (4 mL) and H$_2$O (2 mL), then aq. formaldehyde solution (37%, 0.099 mL, 1.3 mmol) and 9-deazaadenine (0.107 g, 0.80 mmol) added and the mixture heated at 70° C. for 16 h. Silica gel was added to absorb all the solvent then the solvent was evaporated and the residue chromatographed on silica gel (CHCl$_3$-MeOH-28% aq. NH$_4$OH, 85:15:0.5 then 85:15:0.75) to give crude 29 as a colourless gum. Further chromatography (gradient of 0-10% aq. NH$_4$OH (28%) in 2-PrOH) gave 29 (86 mg, 36%) together with a less pure fraction (81 mg, 34%). $^1$H NMR (500 MHz, CD$_3$OD): δ 8.15 (s, 1H), 7.64 (d, J=3.4 Hz, 1H), 7.47 (s, 1H), 7.45 (d, J=3.5 Hz, 1H), 4.03 (ddd, J=6.4, 4.3, 4.3 Hz, 1H), 3.84 (d, J=13.4 Hz, 1H), 3.80 (d, J=13.4 Hz, 1H), 3.41 (dd, J=13.0, 6.3 Hz, 1H), 3.20 (dd, J=13.0, 8.6 Hz, 1H), 3.02 (dd, J=9.7, 7.8 Hz, 1H), 2.90 (dd, J=10.2, 6.5 Hz, 1H), 2.65 (dd, J=10.2, 4.2 Hz, 1H), 2.42 (dd, J=9.8, 6.9 Hz, 1H), 2.34 (m, 1H). $^{13}$C NMR (125.7 MHz, CD$_3$OD, centre line δ 49.0): δ 166.5 (C), 152.1 (C), 151.0 (CH), 147.0 (C), 143.6 (CH), 130.0 (CH), 121.1 (CH), 115.2 (C), 112.5 (C), 76.6 (CH), 62.3 (CH$_2$), 58.4 (CH$_2$), 48.8 (CH$_2$), 48.5 (CH), 38.3 (CH$_2$). ESI-HRMS calcd for C$_{15}$H$_{18}$N$_6$NaOS$_2^+$, (M+Na)$^+$, 385.0876. found 385.0868.

Synthesis of (3R,4S)-1-({4-amino-5H-pyrrolo[3,2-d]pyrimidin-7-yl}methyl)-4-{[(5-{pyridin-4-yl}-1H-1,2,4-triazol-3-yl)thio]methyl}pyrrolidin-3-ol (56) (Scheme 11).

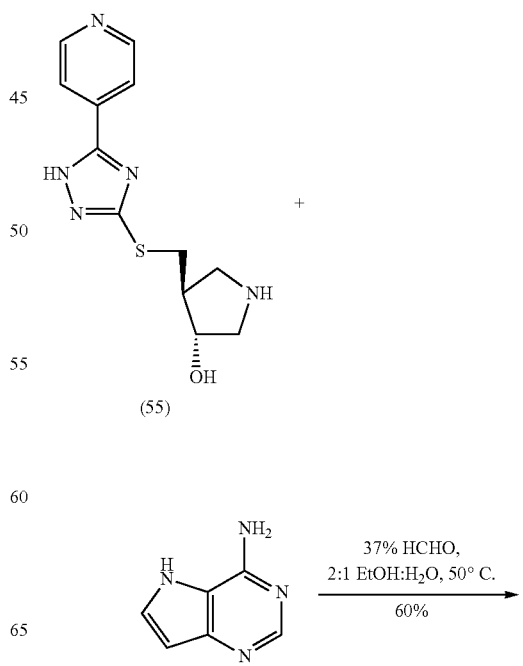

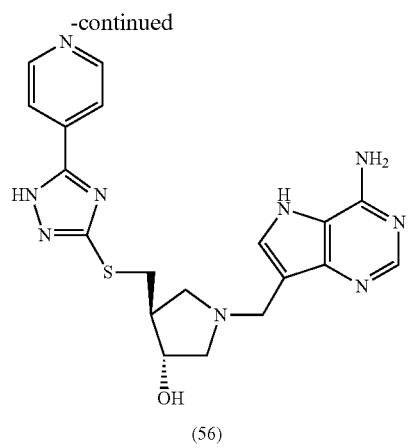

(56)

(3R,4S)-4-({[5-(Pyridin-4-yl)-1H-1,2,4-triazol-3-yl]thio}methyl)pyrrolidin-3-ol (55)

Sodium hydride (69 mg, 1.7 mmol, 60 wt % in oil) was added to a solution of (3R,4S)-tert-butyl-3-hydroxy-4-(methylsulfonyloxymethyl)pyrrolidine-1-carboxylate (3) (300 mg, 1.00 mmol) and 5-(4-pyridyl)-1H-1,2,4-triazole-3-thiol (370 mg, 2.0 mmol) in DMF (5 mL) and the mixture stirred for 1 h. The crude reaction mixture was diluted with $CHCl_3$ and washed with water and brine, dried ($MgSO_4$) and concentrated in vacuo. The crude residue was purified by chromatography (eluent $CHCl_3$=>5%=>10% MeOH in $CHCl_3$) to afford, presumably, (3R,4S)-4-{[(5-(pyridin-4-yl)-1H-1,2,4-triazol-3-yl)thio]methyl}pyrrolidin-3-ol (100 mg, 26%), which was committed to the next step without characterisation. Conc HCl (3 mL) was added to a solution of (3R,4S)-4-{[(5-(pyridin-4-yl)-1H-1,2,4-triazol-3-yl)thio]methyl}pyrrolidin-3-ol (100 mg, 1.2 mmol) in methanol (4 mL) and the mixture concentrated in vacuo. The resulting residue was dissolved in additional conc HCl (2 mL) and concentrated in vacuo, the residue was dissolved in methanol, absorbed onto silica gel and the solid residue purified by chromatography (1%=>25% [7N $NH_3$ in MeOH] in $CHCl_3$) to afford the title compound 55 (72 mg, 26%) as a white solid. $^1$H NMR (500 MHz, $CDCl_3$+$CD_3OD$): δ=8.56 (dd, J=4.7, 1.6 Hz, 2H), 7.96 (dd, J=4.7, 1.6 Hz, 2H), 4.32 (dt, J=5.2, 2.9 Hz, 1H), 3.37 (dd, J=12.4, 5.2 Hz, 1H), 3.34 (quintet, J=1.6 Hz, 1H), 3.26 (dd, J=13.8, 6.7 Hz, 1H), 3.12-3.08 (m, 2H), 3.04 (dd, J=13.9, 8.5 Hz, 1H), and 2.56-2.50 (m, 1H). $^{13}$C NMR (500 MHz, $CD_3OD$): δ=161.0, 157.9, 150.6 (X2), 141.1, 121.8 (X2), 75.4, 53.4, 49.8, 48.9, and 35.1 ppm. ESI-HRMS for $C_{12}H_{16}N_5OS$ [MH]$^+$ calcd 278.1076. found 278.1078.

(3R,4S)-1-({4-Amino-5H-pyrrolo[3,2-d]pyrimidin-7-yl}methyl)-4-({[5-(pyridin-4-yl)-1H-1,2,4-triazol-3-yl]thio}methyl)pyrrolidin-3-ol (56)

Aqueous formaldehyde (24 μL, 0.32 mmol, 37%) was added to a suspension of 9-deazaadenine (22 mg, 0.16 mmol) and compound 55 (45 mg, 0.16 mmol) in a mixture of ethanol (4 mL) and water (2 mL) and the resulting suspension warmed to 50° C. After 2 h the reaction was complete as indicated by TLC analysis. The crude reaction mixture was absorbed onto silica gel and concentrated in vacuo. The solid residue was purified by chromatography (70:29:1=>60:40:2=>5:4:1 $CHCl_3$:MeOH:$NH_4OH$) to afford the title compound 56 (41 mg, 60%) as a white solid. $^1$H NMR (500 MHz, MeOD): δ=8.58 (dd, J=4.7, 1.6 Hz, 2H), 8.16 (s, 1H), 7.95 (dd, J=4.6, 1.6 Hz, 2H), 7.54 (s, 1H), 4.14 (dt, J=6.1, 3.9 Hz, 1H), 4.02 (s, 2H), 3.36 (dd, J=13.4, 6.4 Hz, 1H), 3.31 (quintet, J=1.6 Hz, 1H), 3.25 (dd, J=10.4, 7.7 Hz, 1H), 3.14-3.10 (m, 1H), 2.87 (dd, J=10.9, 3.8 Hz, 1H), 2.69 (dd, J=10.6, 6.9 Hz, 1H), and 2.42 (m, 1H). $^{13}$C NMR (500 MHz, $CD_3OD$): δ=160.6, 157.1, 152.2, 151.2, 150.7 (X2), 146.8, 140.6, 130.7, 121.8 (X2), 115.3, 1104, 75.9, 61.7, 57.9, 49.1, 48.8, and 36.1 ppm. ESI-HRMS for $C_{19}H_{22}N_9OS$ [MH]$^+$ calcd 424.1668. found 424.1662.

RESULTS AND DISCUSSION

BuT-DADMe-ImmA (30) was previously characterized as a transition state analogue inhibitor of EcMTAN (FIG. 1C)[8]. Here, inhibition assays were performed using BuT-DADMe-ImmA against recombinant HpMTAN with 5'-methylthioadenosine as substrate. Purified HpMTAN uses both 5'-methylthioadenosine and 6-amino-6-deoxyfutalosine as facile substrates. The enzyme exhibits high affinity (low $K_m$ values) for both substrates, 0.6±0.3 and 0.8±0.3 μM and $k_{cat}$ values of 12.1±2.3 and 4.3±0.9 respectively. This gives high catalytic efficiency values ($k_{cat}/K_m$) of 2.0×10$^7$ M$^{-1}$s$^{-1}$ for 5'-methylthioadenosine and 5.4×10$^6$ M$^{-1}$s$^{-1}$ for 6-amino-6-deoxy-futalosine. BuT-DADMe-ImmA is a slow-onset tight-binding inhibitor with an initial inhibition constant ($K_i$) of 0.8 nM and following slow-onset of inhibition, an equilibrium dissociation constant ($K_i^*=K_d$) of 36 pM. With a $K_m$ value of 0.8 μM for 6-amino-6-deoxyfutalosine as substrate, the $K_m/K_d$ ratio is 22,200 for this substrate. The low $K_d$ value supports the proposal that BuT-DADMe-ImmA is a transition state analogue inhibitor for HpMTAN. A comparison of the structures of the 5'-methylthioadenosine or S-adenosylhomocysteine substrates for HpMTAN with their transition states (FIG. 1B) shows three features of BuT-DADMe-ImmA that mimic the transition states; a hydroxyl-pyrrolidine moiety, a methylene bridge between the base and sugar, and 9-deazaadenine (FIGS. 1B and 1C). The nitrogen of the hydroxypyrrolidine moiety has a $pK_a$ value of 9, and thus mimics the positive charge of a ribocation at the transition state. The methylene bridge extends the distance between the sugar and the purine base leaving group, as this distance is near 3 Å at the transition state. The 9-deazaadenine alters conjugation in the purine ring, causing an elevated $pK_a$ and protonation of N7, resembling the N7-protonated adenine leaving group at the transition state.

Figures 2A, 2B:
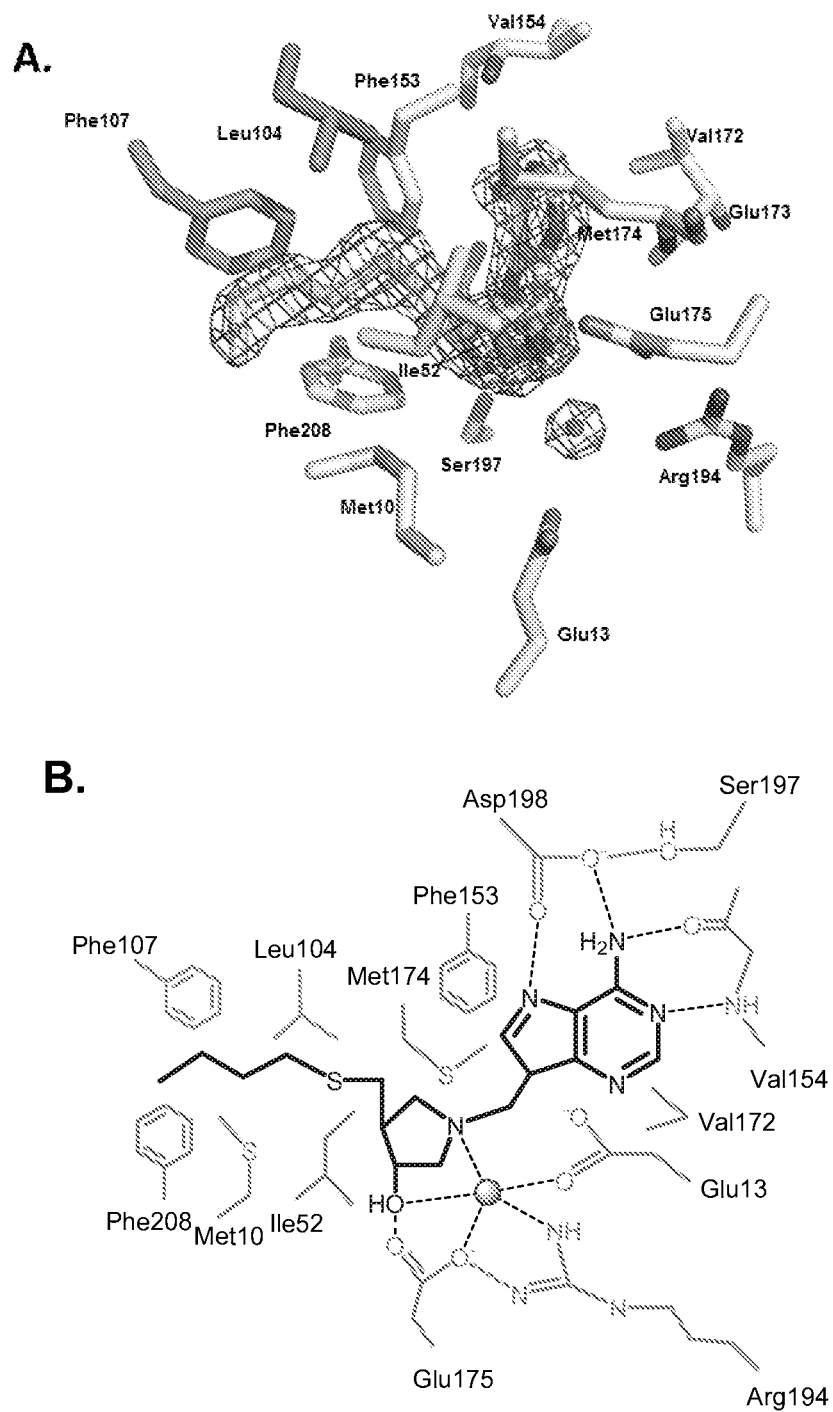
FIG. 2A-2B: Active site of HpMTAN in complex with BuT-DADMe-ImmA (30). A. Crystal structure of the active site of HpMTAN with bound BuT-DADMe-ImmA. The figure shows a 2Fo-Fc map around the inhibitor and catalytic water molecule contoured at 1.5 σ. The graph was generated using Pymol. The crystal structure of HpMTAN in complex with BuT-DADMe-ImmA is deposited under accession code 4FFS in the Protein Data Bank. B. Schematic representation of interactions between BuT-DADMe-ImmA, a water molecule and residues of HpMTAN. The residues Phe 107 and Leu 104 belong to the neighboring monomer of HpMTAN dimer. Dashed lines represent hydrogen bonds. All indicated hydrogen bonds are 3 Å or less except for water to 3'-OH (3.1 Å) and water to Glu175 (3.3 Å).
Figure 4:
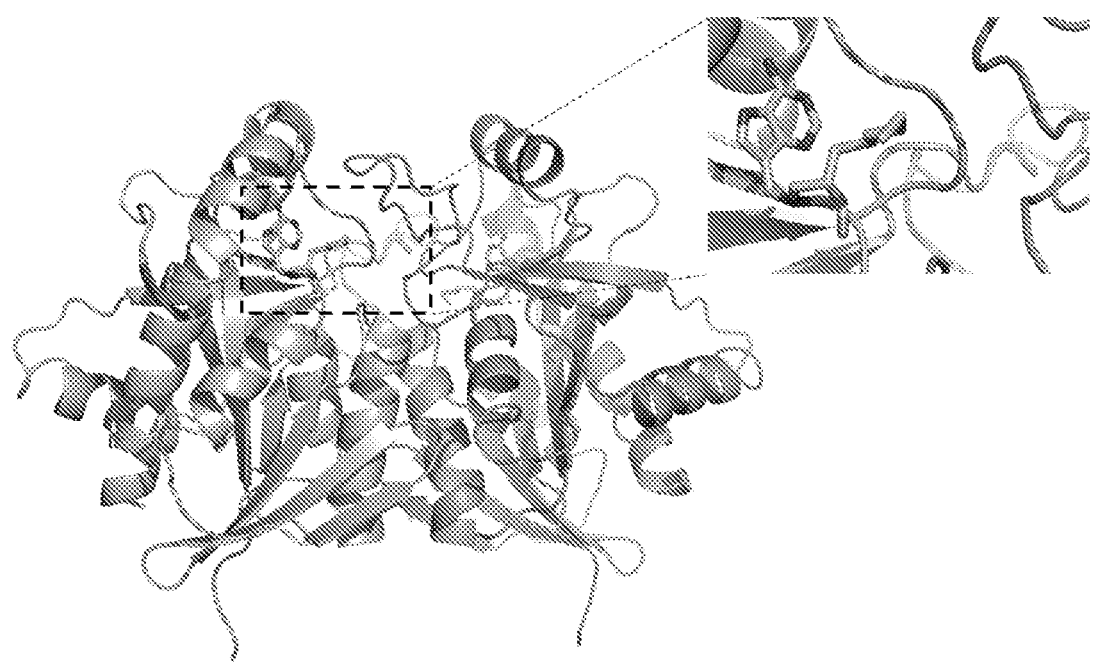
FIG. 4: The crystal structure of HpMTAN bound with BuT-DADMe-ImmA (30). The figure was generated using Pymol.

Catalytic site features involved in tight binding of BuT-DADMe-ImmA (30), were established from the crystal structure of HpMTAN in complex with BuT-DADMe-ImmA (FIG. 2). Like other MTANs, HpMTAN is a homodimer belonging to the superfamily of purine and uridine phosphorylases with the active sites located at the dimer interface (FIG. 4). Adenine binding is stabilized by hydrogen bonds between N7 and OG2 of Asp198, and between N1 and the main chain NH of Val154. The hydrophobic group at the 5'-ribosyl position binding site is not tightly constrained, but is surrounded by a hydrophobic environment, allowing variation at this position (FIGS. 2A and 4). Direct interactions between BuT-DADMe-ImmA and HpMTAN include five hydrogen bonds and a large number of hydrophobic interactions (FIG. 2). The transition state analogue complexes of MTANs include the nucleophilic water molecule in crystal structures and in complexes detected by mass spectrometry in the gas phase[14,15]. In HpMTAN, the nucleophilic water molecule is found 2.6 Å away from the cationic hydroxypyrrolidine nitrogen, the site of water attack in the ribocation transition state (FIG. 2). The water molecule is stabilized in HpMTAN by three hydrogen bonds from protein with two from bound BuT-DADMe-ImmA, contacts clearly contributing to the high affinity of the inhibitor complex.

Figures 3A, 3B:
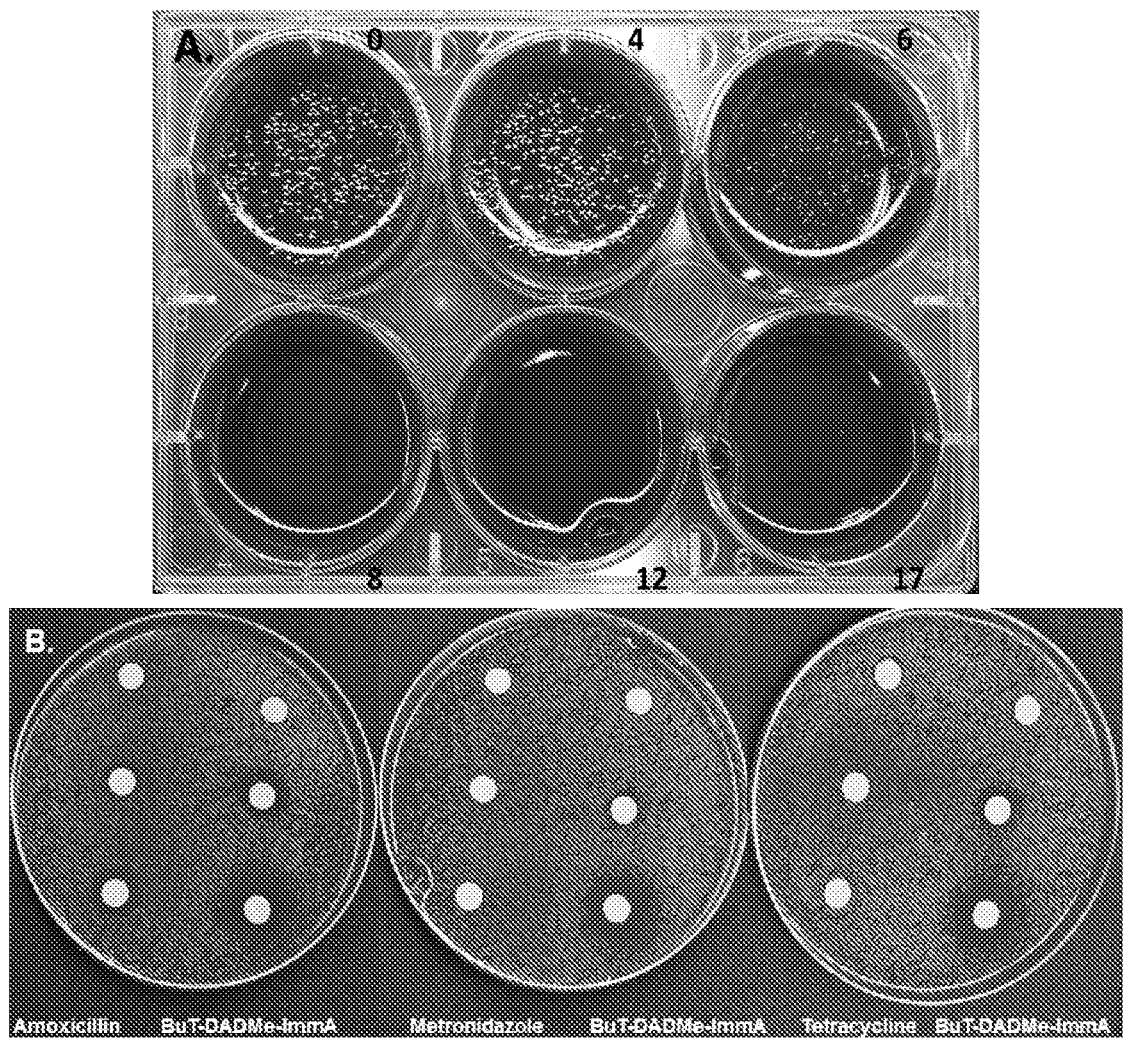
FIG. 3A-3B: The effects of BuT-DADMe-ImmA (30) on *H. pylori* growth. A. The effects of increasing the concentration of BuT-DADMe-ImmA (ng/ml) on growth on blood agar. B. The inhibitory effects of BuT-DADMe-ImmA are compared with amoxicillin, metronidazole and tetracyclin in zone of inhibition studies. Drug concentrations were: 0 (top disc), 10 ng (middle disc) or 20 ng (bottom disc). Each specified antibiotic was applied to the disc in the same manner. Small zones of clearance were seen with 10 ng BuT-DADMe-ImmA (middle right), and large zones at 20 ng (lower right).

The effects of BuT-DADMe-ImmA (30) were tested on *H. pylori* growing on 5% horse blood agar. At 6 ng/ml, slight growth was detected and at 8 ng/ml, no growth was detected, therefore the $MIC_{90}$ value for inhibition of *H. pylori* growth is <8 ng/ml (FIG. 3A). The $MIC_{90}$ value of 8 ng/ml corresponds to a chemical concentration of 23 nM, sufficient to saturate HpMTAN with its $K_d$ value of 36 pM.

Commonly used antibiotics in *H. pylori* infections include amoxicillin, metronidazole and tetracycline. The anti-*H. pylori* effects of BuT-DADMe-ImmA (30) were compared to those antibiotics in common use. The zones of inhibition for BuT-DADMe-ImmA are greater than those for any of the other antibiotics (FIG. 3B). Equivalent amounts of amoxicillin gave a smaller zone of growth inhibition than BuT-DADMe-ImmA, and equivalent amounts of metronidazole or tetracycline gave no growth inhibition. Thus, BuT-DADMe-ImmA is more efficient at inhibition of *H. pylori* growth than commonly used antibiotics.

In most bacteria, MTANs are expressed and catalyze the hydrolysis of the N-ribosidic bonds of 5'-methylthioadenosine and S-adenosylhomocysteine. The two reactions are involved in bacterial quorum sensing, sulfur recycling via S-adenosylmethionine and polyamine synthesis[16]; however, most bacterial MTANs are not essential for bacterial proliferation as judged by planktonic growth conditions. Thus, BuT-DADMe-ImmA (30) did not affect the growth of *E. coli* and *V. cholerae*, although MTAN activity was totally abolished[6]. Likewise, mtn gene deletion in *E. coli* does not affect growth on rich medium but creates biotin auxotrophs[6,17]. The effects BuT-DADMe-ImmA were also tested on the growth for additional clinically common pathogens, *S. aureus, K pneumoniae, S. flexneri, S. enterica* and *P. aeruginosa*. At culture concentrations with BuT-DADMe-ImmA to 5 μg/ml, no growth inhibition was observed for those bacteria, consistent with a non-essential role for their MTANs. Because of the inhibitor specificity for this rare menaquinone pathway, treatment of *H. pylori* infections with BuT-DADMe-ImmA would be unlikely to generate antibiotic resistance in off-target bacterial species.

Bacterial genome analysis predicts the HpMTAN-mediated pathway for menaquinone biosynthesis to be rare, but also to be present in *Campylobacter* species[4]. *Campylobacter jejuni* is the worlds leading cause of bacterial gastroenteritis[18].

The action of HpMTAN is proposed to be in the hydrolysis of 6-amino-6-deoxyfutalosine, and the enzyme was specifically tested for this function. The enzyme shows robust catalytic activity on this with a catalytic efficiency of $5.4 \times 10^6$ $M^{-1}s^{-1}$. The effects of BuT-DADMe-ImmA (30) on the enzyme and growth of *H. pylori* demonstrates a critical role of HpMTAN in *H. pylori*, and supports the proposed pathway of an essential menaquinone biosynthetic pathway for its electron transfer chain or other function[4,19].

Drug resistance has developed quickly in *H. pylori*, and currently, approximately 30% of *H. pylori* infection are resistant to single-agent first line drugs[20]. As a result, the current approach commonly uses triple-agent therapy for *H. pylori* infections and includes two antibiotics with different mechanisms of action. Even with triple-agent therapy, more than 20% of *H. pylori* infections are not readily eradicated[2]. Resistance in the *H. pylori* population is no doubt partially due to exposing *H. pylori* to broad spectrum antibiotics during the treatment of other bacterial infections. In addition, current eradication of *H. pylori* requires antibiotics for two weeks or longer and there is an increase in the development of resistance if treatment is interrupted. The results with BuT-DADMe-ImmA (30) indicate a narrow spectrum antibiotic, with opportunity for use as a single agent or in drug combinations. The other pathogens (*Campylobacter* species) in which MTAN also appears to be essential, are currently treated clinically with ciprofloxacin, erythromycin or azithromycin. BuT-DADMe-ImmA is a more powerful antibiotic for its target in *H. pylori* than common antibiotics, and could be a candidate for *Campylobacter* infections. Thus, BuT-DADMe-ImmA and other HpMTAN inhibitors may serve as specific antibiotics in organisms using MTANs in an essential biosynthetic step. Examples of additional *H. pylori* MTAN inhibitors and their dissociation constants are described in Table 2. Table 3 summarises the dissociation constants versus *H. pylori* MTAN and the MIC90 values against *H. pylori* for specific compounds of the invention. Drug combinations using these compounds may also address current issues of antibiotic resistance.

TABLE 1

Statistics of Data collection, refinement and geometry for HpMTAN bound with BuT-DADMe-ImmA (30). HpMTAN + Butyl-thio-DADMe-Immucillin-A (PDB ID 4FFS)

| Data collection statistics | |
|---|---|
| Space group | P432 |
| Unit cell parameters a (Å) | 157.73 |
| b (Å) | 157.73 |
| c (Å) | 157.73 |
| Temperature (K) | 100 |
| Wavelength (Å) | 1.1001 |
| Resolution (Å) | 50-1.90 (1.93-1.90) |
| Rmerge (%) | 9.9 (61.5) |
| Completeness (%) | 99.9 (100) |
| I/σI | 23.2 (2.9) |
| Unique reflections | 26569 (1301) |
| Redundancy | 7.0 (7.1) |
| Mosaicity (°) | 0.4 |
| B-factor from Wilson plot (Å²) | 23 |
| Refinement statistics | |
| Resolution (Å) | 42.19-1.90 |
| Total number of reflections | 26549 |
| Working set: number of reflections | 25229 |
| $R_{factor}$ (%) | 16.12 |
| Test set: number of reflections | 1320 |
| $R_{free}$ (%) | 19.16 |
| Protein atoms | 1818 |
| Water atoms | 229 |
| BuT-DADMe-ImmA atoms | 23 |
| Chloride | 1 |
| Geometry statistics | |
| Rmsd (bond distance) (Å) | 0.01 |
| Rmsd (bond angle) (°) | 1.39 |
| Rmsd B | |
| Main chain atoms (Å²) | 0.85 |
| Side chain atoms (Å²) | 1.81 |
| Average B | |
| Main chain atoms (Å²) | 23.07 |
| Side chain atoms (Å²) | 27.87 |
| Water atoms (Å²) | 35.52 |
| BuT-DADMe-ImmA atoms (Å²) | 21.94 |
| Chloride (Å²) | 37.65 |

TABLE 1-continued

Statistics of Data collection, refinement and geometry for HpMTAN bound with BuT-DADMe-ImmA (30). HpMTAN + Butyl-thio-DADMe-Immucillin-A (PDB ID 4FFS)

Ramachandran plot

| | |
|---|---|
| Ramachandran favored (%) | 96.5 |
| Ramachandran outliers (%) | 0 |

TABLE 2

H. pylori MTAN inhibitors and their dissociation constants. The compounds are described in [32-35].

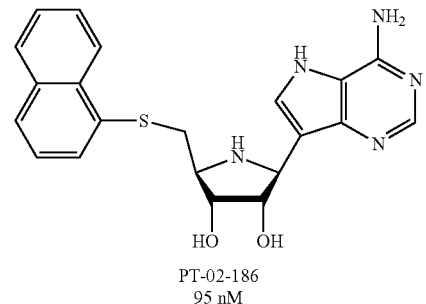

PT-02-186
95 nM

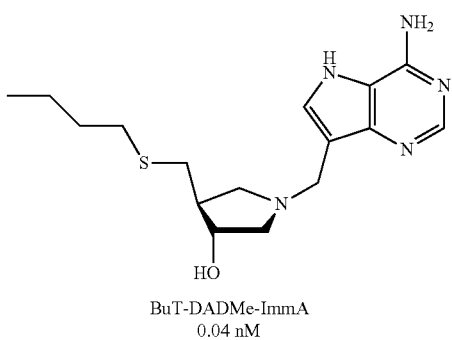

BuT-DADMe-ImmA
0.04 nM

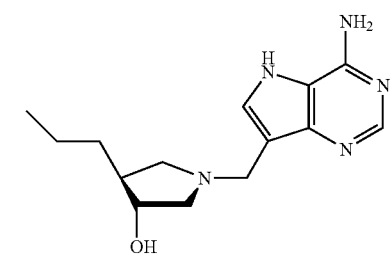

DHL-159
0.01 nM

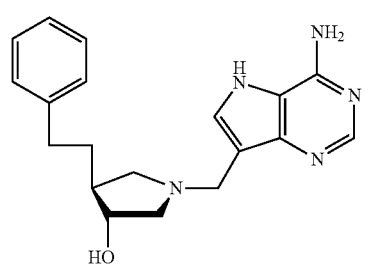

DHL140
254 nM

TABLE 2-continued

H. pylori MTAN inhibitors and their dissociation constants. The compounds are described in [32-35].

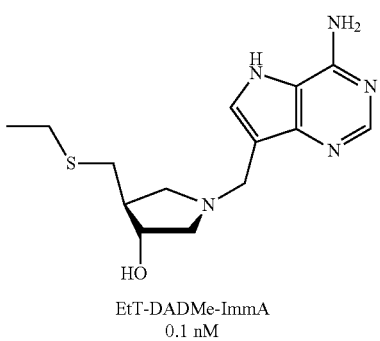

EtT-DADMe-ImmA
0.1 nM

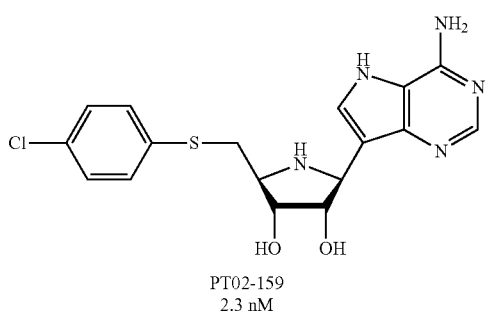

PT02-159
2.3 nM

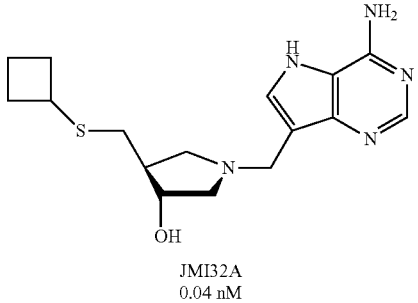

JMI32A
0.04 nM

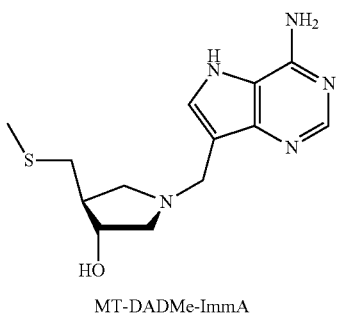

MT-DADMe-ImmA
0.1 nM

TABLE 2-continued
*H. pylori* MTAN inhibitors and their dissociation constants.
The compounds are described in [32-35].
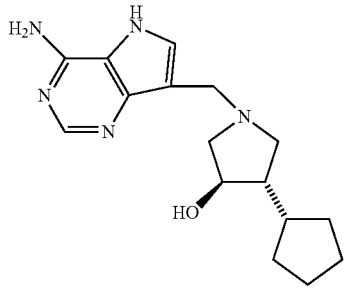
AIL901 48b
(racemic)
0.41 nM
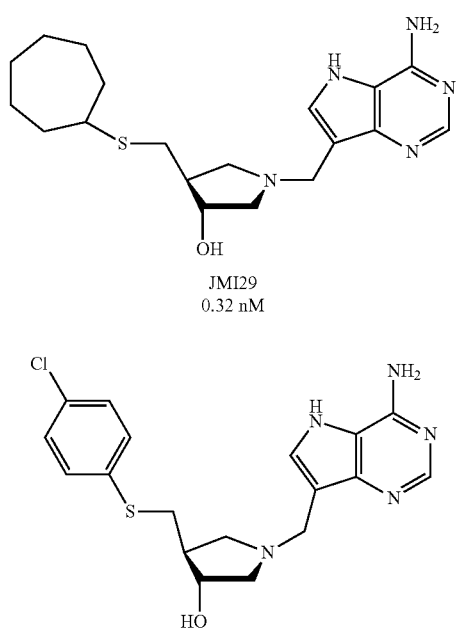
JMI29
0.32 nM
pClPhT-DADMe-ImmA
0.1 nM
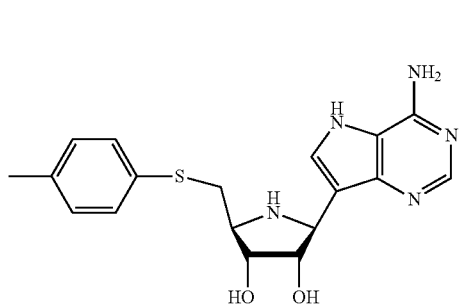
PT02-158
2.6 nM
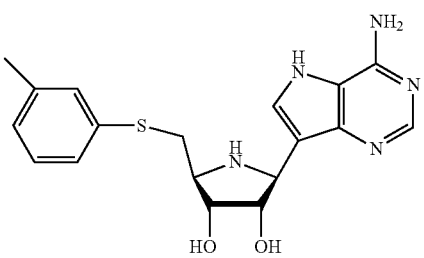
PT02-165
2.1 nM
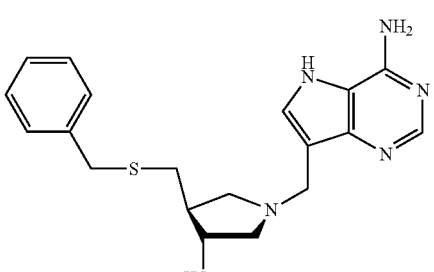
GBEB865A
0.31 nM
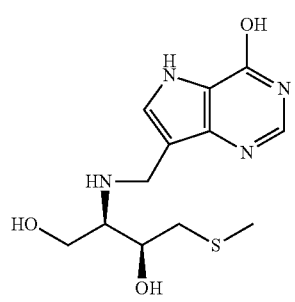
JMI-579
>2000 nM

TABLE 3

Substituted DADMe-Immucillin-A Inhibitors of *Helicobacter pylori* MTAN and their MIC90 values against *H. pylori*.

| Compound number, Z =, Origin | Inhibition of *H. pylori* MTAN | | Inhibition of *H. pylori* growth |
|---|---|---|---|
| | $K_i$ (nM) | $K_i^*$ (nM) | MIC90 (ng/mL) |
| (30) n-BuS- (Synthesis in reference 21) | 0.79 ± 0.04 (Reference 10) | 0.036 ± 0.002 (Reference 10) | 6-8 |
| (14) Hex-5-yn-1-ylthio- | 0.5 ± 0.2 | 0.09 ± 0.02 | 4-8 |
| (18) n-Hexylthio- | 0.21 ± 0.03 | 0.005 ± 0.002 | 4-8 |
| (31) MeS- (Synthesis in reference 21) | 1.2 (Reference 10) | 0.57 (Reference 10) | 6-12 |
| (32) Cyclopentylthio- (Synthesis in reference 8) | 0.78 ± 0.15 | 0.17 ± 0.01 | 7-14 |
| (27) Pyrazin-2-ylthio- | 0.043 ± 0.001 | 0.006 ± 0.00 | 8 |
| (33) n-Propyl- (Synthesis in reference 7) | 0.058 ± 0.014 | 0.007 ± 0.002 | 10 |
| (34) EtS- (synthesis in reference 21) | 0.12 ± 0.03 | 0.52 ± 0.04 | 16 |
| (35) Ethyl- (Synthesis in reference 21) | 0.053 ± 0.007 | | 16 |

TABLE 3-continued

Substituted DADMe-Immucillin-A Inhibitors of *Helicobacter pylori* MTAN and their MIC90 values against *H. pylori*.

| Compound number, Z =, Origin | Inhibition of *H. pylori* MTAN | | Inhibition of *H. pylori* growth |
|---|---|---|---|
| | Ki (nM) | Ki* (nM) | MIC90 (ng/mL) |
| (36) Cylcohexylmethylthio- (Synthesis in reference 8) | 0.56 ± 0.27 | 0.045 ± 0.004 | 18-35 |
| (12) 4-Hydroxybutylthio- | 0.34 ± 0.07 | 0.11 ± 0.04 | 20 |
| (29) Thiazol-2-ylthio- | 0.24 ± 0.07 | 0.016 ± 0.005 | 20 |
| (13) HOCH$_2$CH$_2$OCH$_2$CH$_2$S— | 0.96 ± 0.16 | 0.015 ± 0.004 | 35-70 |
| (37) Cycloheptylthio- (Synthesis in reference 8) | 0.40 ± 0.05 | 0.027 ± 0.002 | 35-70 |
| (11) 3-Hydroxypropylthio- | 0.89 ± 0.13 | 0.10 ± 0.01 | 40 |
| (38) BnS- (Synthesis in reference 21) | 203 ± 28 | 0.31 ± 0.08 | 40 |
| (19) n-Hexylthiomethyl- | 0.7 ± 0.1 | 0.14 ± 0.01 | 40 |
| (24) Pyridin-2-ylthio- | 0.32 ± 0.7 | 0.041 ± 0.002 | 40 |
| (16) HOCH$_2$CH$_2$SCH$_2$— | 0.26 ± 0.03 | 0.05 ± 0.01 | 80 |
| (17) HOCH$_2$CH$_2$OCH$_2$CH$_2$SCH$_2$— | 0.28 ± 0.03 | 0.05 ± 0.01 | 80 |
| (40) Cyclobutylthio- (Synthesis in reference 8) | 0.27 ± 0.04 | 0.04 ± 0.01 | |
| (10) HOCH$_2$CH$_2$S— | 0.43 ± 0.12 | 0.04 ± 0.01 | |
| (41) p-Chlorophenylthio- (Synthesis in reference 21) | 40 (reference 10) | 0.57 | |
| (56) [5-(Pyridin-4-yl)-1H-1,2,4-triazol-3-yl]thio- | 0.28 ± 0.02 (Note 1) | | >100 |

Note 1:
This compound had low solubility in water that may affect the accuracy of the listed Ki value and its effectiveness in the agar plate *H. pylori* inhibition assay.

TABLE 4

Substituted Immucillin-A Inhibitors of *Helicobacter pylori* MTAN and their MIC90 values against *H. pylori*.

| Compound number, Z =, Origin | Inhibition of *H. pylori* MTAN | | Inhibition of *H. pylori* growth |
|---|---|---|---|
| | Ki (nM) | Ki* (nM) | MIC90 (ng/mL) |
| (42) n-PrS- (Synthesis in reference 36) | 0.6 ± 0.1 | | 16 |
| (43) BuS- (Synthesis in reference 36) | 0.51 ± 0.07 | 0.05 ± 0.01 | 20 |
| (44) MeS- (Synthesis in reference 36) | 0.98 ± 0.06 | 0.24 ± 0.03 | 80 |

REFERENCES

1. Kuipers, E. J., Thijs, J. C. & Festen, H. P. *Aliment. Pharm. Therap.* 9 Suppl 2, 59-69 (1995).
2. Malfertheiner, P. et al. *Lancet* 377, 905-913 (2011).
3. Popp, J. L., Berliner, C. & Bentley, R. *Anal. Biochem.* 178, 306-310 (1989).
4. Li, X., Apel, D., Gaynor, E. C. & Tanner, M. E. *J. Biol. Chem.* 286, 19392-19398 (2011).
5. Dairi, T. *J. Antibiot.* 62, 347-352 (2009).
6. Gutierrez, J. A. et al. *Nature Chem. Biol.* 5, 251-257 (2009).
7. Longshaw, A. I., Adanitsch, F., Gutierrez, J. A., Evans, G. B., Tyler, P. C., Schramm, V. L. Design and Synthesis of Potent "Sulfur-Free" Transition State Analogue Inhibitors of 5'-Methylthioadenosine Nucleosidase and 5'-Methylthioadenosine Phosphorylase. *J. Med. Chem.* 53, 6730-6746 (2010).
8. Singh, V. et al. Femtomolar transition state analogue inhibitors of 5'-methylthioadenosine/S-adenosylhomocysteine nucleosidase from *Escherichia coli*. *J. Biol. Chem.* 280, 18265-18273 (2005).
9. Singh, V. & Schramm, V. L. *J. Am. Chem. Soc.* 129, 2783-2795 (2007).
10. Gutierrez, J. A. et al. Picomolar inhibitors as transition-state probes of 5'-methylthioadenosine nucleosidases. *ACS Chem. Biol.* 2, 725-734 (2007).
11. Wolfenden, R. *Nature* 223, 704-705 (1969).
12. Radzicka, A. & Wolfenden, R. *Science* 267, 90-93 (1995).
13. Schramm, V. L. *Ann. Rev. Biochem.* 80, 703-732 (2011).
14. Wang, S. et al. *J. Am. Chem. Soc.* 134, 1468-1470 (2012).
15. Singh, V., Lee, J. E., Nunez, S., Howell, P. L. & Schramm, V. L. *Biochemistry* 44, 11647-11659 (2005).
16. Parveen, N. & Cornell, K. A. *Mol. Microbiol.* 79, 7-20 (2011).
17. Choi-Rhee, E., & Cronan, J. E. *Chem. Biol.* 12, 589-593 (2005).
18. Man, S. M. *Nat. Rev. Gastroenterol. Hepatol.* 8, 669-685 (2011)
19. Marcelli, S. W. et al. *FEMS Microbiol. Lett.* 138, 59-64 (1996).
20. Vakil, N. *Am. J. Gastro.* 104, 26-30 (2009).
21. Evans, G. B. et al. Second generation transition state analogue inhibitors of human 5'-methylthioadenosine phosphorylase. *J. Med. Chem.* 48, 4679-4689 (2005).
22. Xu, L., Apel, D., Gaynor, E. C., & Tanner, M. E. 5'-Methylthioadenosine nucleosidase is implicated in playing a key role in a modified futalosine pathway for menzquinone biosynthesis in *Campylobacter jejuni*. *J. Biol. Chem.* 286, 19392-19398 (2011).
23. Minor, W., Cymborowski, M., Otwinowski, Z. & Chruszcz, M. HKL-3000: the integration of data reduction and structure solution—from diffraction images to an initial model in minutes. *Acta crystallographica. Section D, Biol. Cryst.* 62, 859-86, (2006).
24. Vagin, A. & Teplyakov, A. Molecular replacement with MOLREP. *Acta Cryst.* D66, 22-25, (2010).

25. The CCP4 suite: programs for protein crystallography. *Acta Cryst.* D50, 760-763 (1994).
26. Potterton, E., Briggs, P., Turkenburg, M. & Dodson, E. A graphical user interface to the CCP4 program suite. *Acta Cryst.* D59, 1131-1137 (2003).
27. Emsley, P. & Cowtan, K. Coot: model-building tools for molecular graphics. *Acta Cryst.* D60, 2126-2132 (2004).
28. Murshudov, G. N., Vagin, A. A. & Dodson, E. J. Refinement of macromolecular structures by the maximum-likelihood method. *Acta Cryst.* D53, 240-255 (1997).
29. Laskowski, R. A., Macarthur, M. W., Moss, D. S. & Thornton, J. M. Procheck—a program to check the stereochemical quality of protein structures. *J. Appl. Crystallogr.* 26, 283-291 (1993).
30. Chen, V. B. et al. MolProbity: all-atom structure validation for macromolecular crystallography. *Acta Cryst.* D66, 12-21 (2010).
31. Davis, I. W. et al. MolProbity: all-atom contacts and structure validation for proteins and nucleic acids. *Nucleic Acids Res.* 35, W375-383 (2007).
32. U.S. Pat. No. 7,098,334, Furneaux et al., issued Aug. 29, 2006.
33. U.S. Pat. No. 7,553,839, Evans et al., issued Jun. 30, 2009.
34. U.S. Patent Application Publication No. 2012/0157479, Evans et al., published Jun. 21, 2012.
35. U.S. Patent Application Publication No. 2011/0046167, Clinch et al., published Feb. 24, 2011.
36. Evans, G. B. et al, *J. Med. Chem.*, 47, 3275-3281 (2004).
37. Clinch, K.; Evans, G. B.; Furneaux, R. H.; Lenz, D. H.; Mason, J. M.; Mee, S. P. H.; Tyler, P. C.; Wilcox, S. *Org. Biomol. Chem.*, 5, 2800-2802 (2007).

What is claimed is:

1. A compound selected from the group consisting of

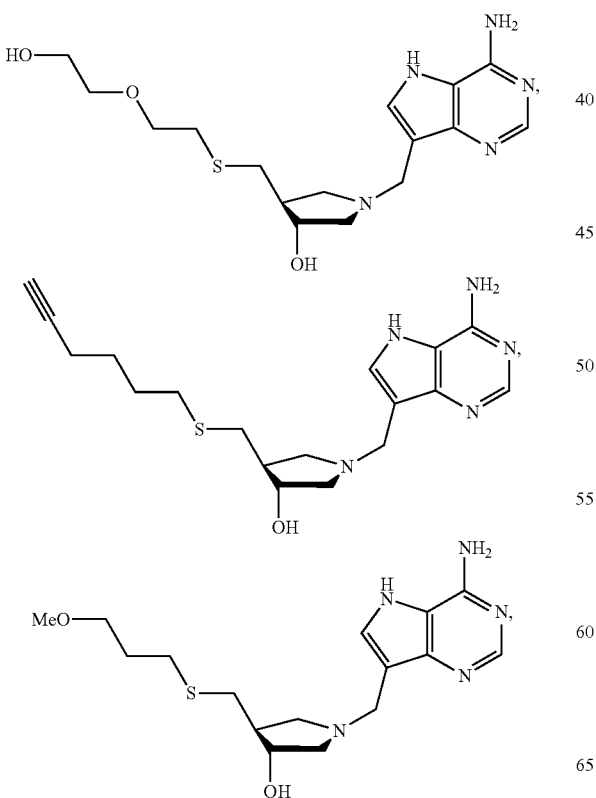

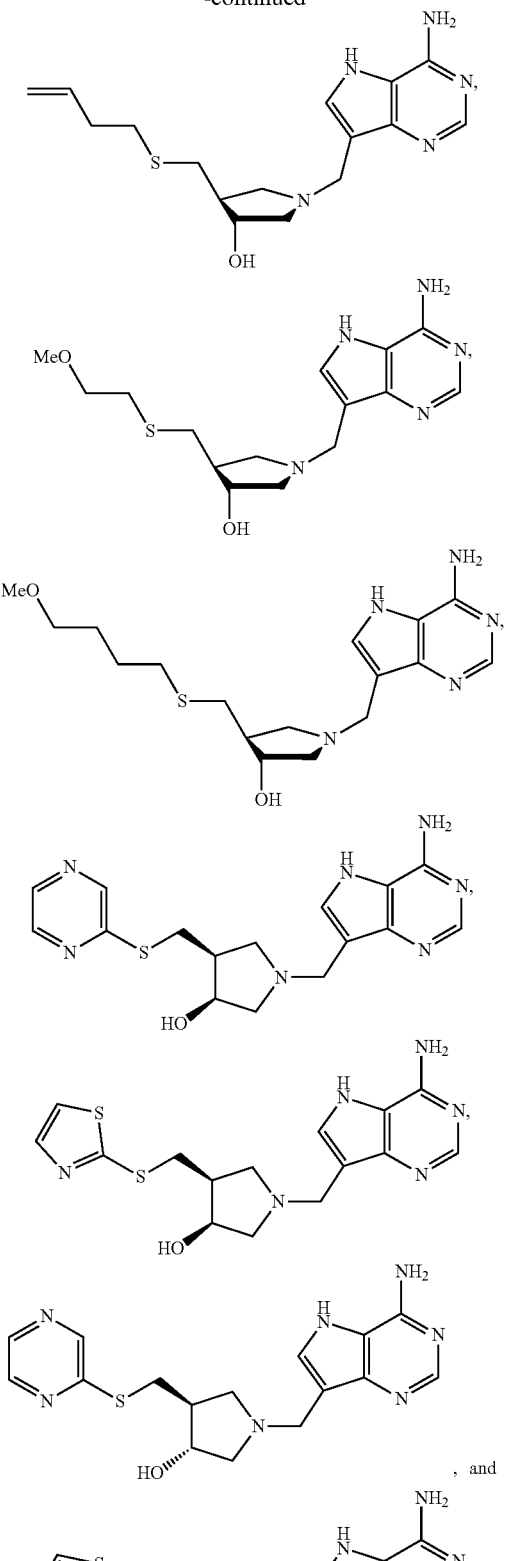

, and or a pharmaceutically acceptable salt thereof, or an ester thereof.

2. A pharmaceutical composition comprising a compound of claim 1 and a pharmaceutically acceptable carrier.

3. A method of treating a *Helicobacter pylori* (*H. pylori*) infection in a subject in need thereof comprising administering to the subject a compound of claim 1 in an amount effective to inhibit growth of *H. pylori*.

4. The method of claim 3, wherein the subject has a peptic ulcer.

5. The method of claim 3, wherein the subject has a gastric ulcer or a duodenal ulcer.

6. The method of claim 3, wherein the compound is administered orally.

* * * * *

UNITED STATES PATENT AND TRADEMARK OFFICE
CERTIFICATE OF CORRECTION

Page 1 of 1

PATENT NO. : 11,186,575 B2
APPLICATION NO. : 14/419669
DATED : November 30, 2021
INVENTOR(S) : Vern L. Schramm et al.

It is certified that error appears in the above-identified patent and that said Letters Patent is hereby corrected as shown below:

On the Title Page

In (71) Applicants, "Albert Einstein College of Medicine, Inc." should read --Albert Einstein College of Medicine--

In (73) Assignees, "Alber Einslein College of Medicine" should read --Albert Einstein College of Medicine--

Signed and Sealed this
First Day of March, 2022

Drew Hirshfeld
*Performing the Functions and Duties of the*
*Under Secretary of Commerce for Intellectual Property and*
*Director of the United States Patent and Trademark Office*